US009708297B2

(12) United States Patent
Coates et al.

(10) Patent No.: US 9,708,297 B2
(45) Date of Patent: Jul. 18, 2017

(54) CGRP RECEPTOR ANTAGONISTS

(71) Applicant: Eli Lilly and Company, Indianapolis, IN (US)

(72) Inventors: David Andrew Coates, New Palestine, IN (US); Kevin Charles Fortner, Indianapolis, IN (US); Steven Marc Massey, Indianapolis, IN (US); Jason Kenneth Myers, Indianapolis, IN (US); Antonio Navarro, Indianapolis, IN (US); Miles Goodman Siegel, Indianapolis, IN (US); Russell Dean Stucky, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/229,249

(22) Filed: Aug. 5, 2016

(65) Prior Publication Data
US 2017/0044138 A1    Feb. 16, 2017

Related U.S. Application Data

(60) Provisional application No. 62/266,867, filed on Dec. 14, 2015, provisional application No. 62/203,996, filed on Aug. 12, 2015.

(51) Int. Cl.
| | | |
|---|---|---|
| C07D 401/14 | (2006.01) | |
| C07C 309/04 | (2006.01) | |
| C07D 401/12 | (2006.01) | |

(52) U.S. Cl.
CPC .......... C07D 401/14 (2013.01); C07C 309/04 (2013.01); C07D 401/12 (2013.01); C07B 2200/13 (2013.01)

(58) Field of Classification Search
None
See application file for complete search history.

(56) References Cited

U.S. PATENT DOCUMENTS

| | | | |
|---|---|---|---|
| 6,680,387 B2 | 1/2004 | Druzgala et al. | |
| 2015/0203496 A1* | 7/2015 | Bell ..................... | C07D 471/20 514/278 |

OTHER PUBLICATIONS

Pending U.S. Appl. No. 15/229,229, filed Aug. 5, 2016; Inventors: David Andrew Coates, Kevin Charles Fortner, Richard Duane Johnston, Steven Marc Massey, Jason Kenneth Myers, Qing Shi, and Miles Goodman Siegel; Applicant, Eli Lilly and Company.
CAS 1390111-26-8 (Commercial Sources: Aurora Building Blocks, Order No. A20.893.332; Aurora Fine Chemicals LLC 7929 Silverton Ave., Suite 609, San Diego, CA 92126, U.S.; Aurora Screening Library Order No. K12.211.235; Aurora Fine Chemicals LLC7929 Silverton Ave., Suite 609, San Diego, CA 92126, U.S.).
CAS 1376302-01-0 (Commercial Sources: Aurora Screening Library, Order No. K11.266.151; Aurora Fine Chemicals LLC, 7929 Silverton Ave., Suite 609, San Diego, CA 92126, U.S.; Enamine HTS Collection, Order No. Z1255568116; Enamine LLC 2940 Glendale Milford Road, Suite 410, Cincinnati, OH 45241-3131, U.S.).
CAS 1573422-88-4; 4-[(2,5-dioxo-3-pyrrolidinyl)methy1]-N-[[4-[(methylamino)methyl]phenyl]methyl]-benzamide; Mar. 25, 2014; [SciFinder], [retrieved on Apr. 26, 2017]. Retrieved from the Internet <URL: https://scifinder.cas.org/scifinder/view/scifinder/scifinderExplore.jsf>.
CAS 1572972-10-1; 4-[(2,5-dioxo-3-pyrrolidinyl)methyl]-N-[[4-[(methylamino)methyl]phenyl]methyl]-benzamide; Mar. 25, 2014; [SciFinder], [retrieved on Apr. 26, 2017]. Retrieved from the Internet <URL: https://scifinder.cas.org/scifinder/view/scifinder/scifinderExplore.jsf>.

* cited by examiner

*Primary Examiner* — Brian J Davis
(74) *Attorney, Agent, or Firm* — Nelsen L. Lentz

(57) ABSTRACT

The present invention provides a compound of Formula II:

Formula II or a pharmaceutically acceptable salt thereof.

23 Claims, No Drawings

CGRP RECEPTOR ANTAGONISTS

The present invention relates to certain novel calcitonin gene-related peptide (CGRP) receptor antagonist compounds, to pharmaceutical compositions comprising the compounds, to methods of using the compounds to prevent or treat certain physiological disorders such as migraine, and to intermediates and processes useful in the synthesis of the compounds.

The present invention is in the field of prevention and treatment of migraine and other neurological diseases and disorders thought to be mediated by CGRP (See for example, S. Benemei, et. al., *Current Opinion in Pharmacology*, 9, 9-14 (2009)). Migraine is a debilitating disease suffered by millions of people worldwide. Treatment options for migraine include the triptans, such as sumatriptan and zolmitriptan. Unfortunately, currently approved agents available to the patient do not always provide effective treatment, and these agents can be associated with various untoward side effects such as dizziness, paresthesia, and chest discomfort. In addition, triptans possess certain cardiovascular concerns causing them to be contraindicated in patients suffering from substantial underlying cardiovascular disease or uncontrolled hypertension (See T. W. Ho, et. al., *The Lancet*, 372, 2115-2123 (2008)). Thus, there is a significant unmet need in the prevention and treatment of migraine. CGRP receptor antagonists are desired to provide more effective treatment for or prevention of certain neurological diseases, such as migraine.

U.S. Pat. No. 6,680,387 discloses certain 5-benzyl- or 5-benzylidene-thiazolidine-2,4-diones for the treatment of type-II diabetes mellitus, atherosclerosis, hypercholesterolemia, and hyperlipidemia.

The present invention provides certain novel compounds that are antagonists of the CGRP receptor. Furthermore, the present invention provides certain novel compounds that are antagonists of the CGRP receptor which have the potential for an improved side-effect profile in the treatment or prevention of migraine.

Accordingly, the present invention provides a compound of Formula II:

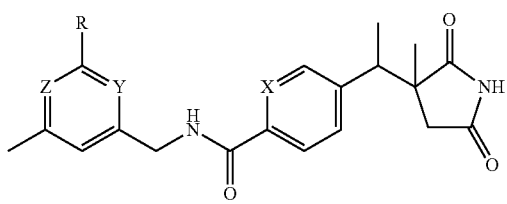

Formula II wherein

Y is CH or N;

Z is CH or N;

provided that when Y is CH, Z is N and when Y is N, Z is CH;

X is CH or N; and

R is C1-C3 alkyl, C3-C5 cycloalkyl, or CN, or a pharmaceutically acceptable salt thereof.

The present invention further provides a compound of Formula I:

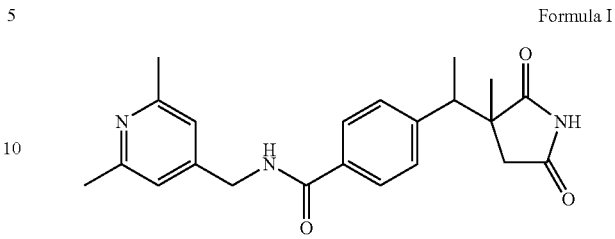

Formula I or a pharmaceutically acceptable salt thereof.

The present invention also provides a method of preventing migraine in a patient, comprising administering to a patient in need thereof an effective amount of a compound of Formula I or Formula II, or a pharmaceutically acceptable salt thereof.

The present invention further provides a method of treating migraine in a patient, comprising administering to a patient in need thereof an effective amount of a compound of Formula I or Formula II, or a pharmaceutically acceptable salt thereof. The present invention also provides a method of antagonizing the CGRP receptor in a patient, comprising administering to a patient in need thereof an effective amount of a compound of Formula I or Formula II, or a pharmaceutically acceptable salt thereof.

Furthermore, this invention provides a compound of Formula I or Formula II, or a pharmaceutically acceptable salt thereof for use in therapy, in particular for the treatment of migraine. In addition, this invention provides a compound of Formula I or Formula II, or a pharmaceutically acceptable salt thereof for use in preventing migraine. Even furthermore, this invention provides the use of a compound of Formula I or Formula II, or a pharmaceutically acceptable salt thereof, for the manufacture of a medicament for the treatment of migraine or for preventing migraine.

The invention further provides a pharmaceutical composition, comprising a compound of Formula I or Formula II, or a pharmaceutically acceptable salt thereof, with one or more pharmaceutically acceptable carriers, diluents, or excipients. The invention further provides a process for preparing a pharmaceutical composition, comprising admixing a compound of Formula I or Formula II, or a pharmaceutically acceptable salt thereof, with one or more pharmaceutically acceptable carriers, diluents, or excipients. This invention also encompasses novel intermediates and processes for the synthesis of the compounds of Formula I and Formula II.

As used herein, the term "C1-C3 alkyl" refers to a methyl, ethyl, propyl, and isopropyl group.

As used herein, the term "C3-C5 cycloalkyl" refers to a cyclopropyl, cyclobutyl, and cyclopentyl group.

As used herein, the terms "treating", "treatment", or "to treat" includes restraining, slowing, stopping, or reversing the progression or severity of an existing symptom or disorder.

As used herein, the term "preventing" or "prevention" refers to protecting a patient who is prone to a certain disease or disorder, such as migraine, but is not currently suffering from symptoms of the disease or disorder, such as symptoms of migraine.

As used herein, the term "patient" refers to a mammal, in particular a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are generally effective over a wide dosage range. For example, dosages per day normally fall within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present invention are preferably formulated as pharmaceutical compositions administered by any route which makes the compound bioavailable, including oral and transdermal routes. Most preferably, such compositions are for oral administration. Such pharmaceutical compositions and processes for preparing same are well known in the art. (See, e.g., Remington: The Science and Practice of Pharmacy; D. B. Troy, Editor, 21st Edition, Lippincott, Williams & Wilkins, 2006).

The compounds of Formula I and Formula II, or pharmaceutically acceptable salts thereof are particularly useful in the prevention and treatment methods of the invention, but certain groups, substituents, and configurations are preferred. The following paragraphs describe such preferred groups, substituents, and configurations. Although the present invention contemplates all individual enantiomers and diastereomers, as well as mixtures of the enantiomers of said compounds, including racemates, the compounds with absolute configuration as set forth below are especially preferred. It is understood that these preferences are applicable both to the prevention and treatment methods and to the new compounds of the invention.

Compounds of Formula III:

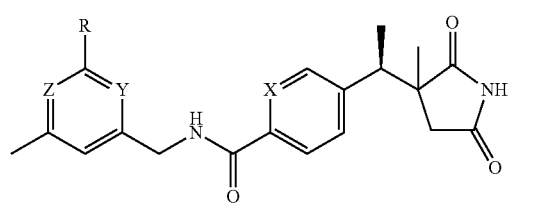 [SMILES: Cc1cc(CNC(=O)c2ccc([C@@H](C)[C@]3(C)CC(=O)NC3=O)cc2)cc(C)n1]

Formula III or pharmaceutically acceptable salts thereof are preferred.

Compounds of Formula IV:

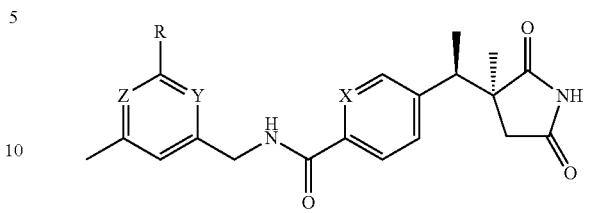

Formula IV or pharmaceutically acceptable salts thereof, are further preferred. In addition, compounds or salts of Formulas I, II, III and IV wherein X is CH are preferred. Compounds or salts of Formulas I, II, III, and IV wherein Y is CH and Z is N are further preferred. Compounds or salts of Formulas I, II, III, and IV wherein R is C1-C3 alkyl are further preferred with methyl being especially preferred.

The following compounds are more preferred:

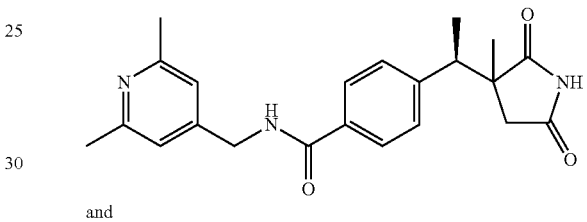

and

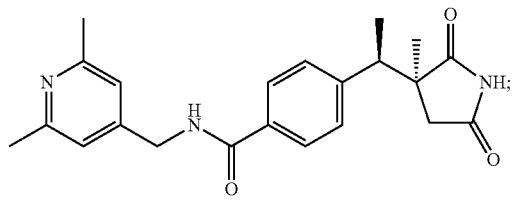

and the pharmaceutically acceptable salts thereof.

The following compound is particularly preferred:

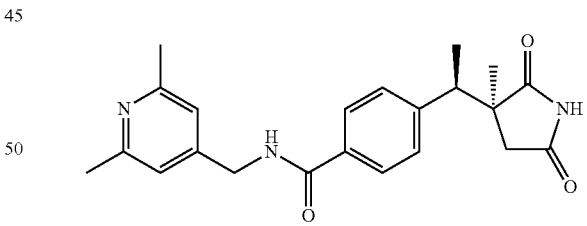

and the pharmaceutically acceptable salts thereof, with the corresponding free base being especially preferred, and a crystalline anhydrate of the corresponding free base which is characterized by a substantial peak in the X-ray diffraction spectrum at diffraction angle 2-theta of 13.4°, in combination with one or more of the peaks selected from the group consisting of 14.4°, 18.1°, 19.4°, 20.9°, 21.2°, 21.5° and 26.5°, with a tolerance for the diffraction angles of 0.2 degrees, is most especially preferred.

N-[(2,6-dimethylpyridin-4-yl)methyl]-4-{(1R)-1-[(3S)-3-methyl-2,5-dioxopyrrolidin-3-yl]ethyl}benzamide methanesulfonate is a particularly preferred compound. Crystalline N-[(2,6-dimethylpyridin-4-yl)methyl]-4-{(1R)-1-[(3S)-3- methyl-2,5-dioxopyrrolidin-3-yl]ethyl}benzamide methanesulfonate which is characterized by a substantial peak in the X-ray diffraction spectrum at diffraction angle 2-theta of at 18.8° in combination with one or more of the peaks selected from the group consisting of 23.2°, 24.7°, and 15.2°; with a tolerance for the diffraction angles of 0.2 degrees is especially preferred.

Additionally, certain intermediates described in the following preparations may contain one or more nitrogen protecting groups. It is understood that protecting groups may be varied as appreciated by one of skill in the art depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Individual isomers, enantiomers, and diastereomers may be separated or resolved by one of ordinary skill in the art at any convenient point in the synthesis of compounds of the invention, by methods such as selective crystallization techniques or chiral chromatography (See, for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994).

A pharmaceutically acceptable salt of the compounds of the invention, such as a hydrochloride salt, can be formed, for example, by reaction of an appropriate free base of a compound of the invention, an appropriate pharmaceutically acceptable acid such as hydrochloric acid in a suitable solvent such as diethyl ether under standard conditions well known in the art. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

Certain abbreviations are defined as follows: "ACN" refers to acetonitrile; "BOP" refers to (benzotriazol-1-yloxy)tris(dimethylamino)phosphonium hexafluorophosphate; "c-Bu" refers to cyclobutyl; "c-Pr" refers to cyclopropyl; "DCM" refers to DCM or methylene chloride; "DMEA" refers to N,N-dimethylethylamine; "DIPEA" refers to N,N-diisopropylethylamine; "DMF" refers to N,N-dimethylformamide; "DMSO" refers to dimethylsulfoxide; "EDCI" refers to 1-ethyl-3-(3-dimethylaminopropyl)carbodiimide; "Et" refers to ethyl; "Et$_2$O" refers to diethyl ether; "EtOAc" refers to ethyl acetate; "EtOH" refers to ethanol; "HOAT" refers to 1-hydroxy-7-azabenzotriazole; "HATU" refers to N-[(dimethylamino)-1H-1,2,3-triazolo-[4,5-b]pyridin-1-ylmethylene]-N-methylmethanaminium hexafluorophosphate N-oxide; "HPLC" refers to high Performance Liquid Chromatography; "HOBt" refers to hydroxybenzotriazole; "hr" refers to hour or hours; "HTRF" refers to Homogeneous Time Resolved Fluorescence; "IC$_{50}$" refers to the concentration of an agent that produces 50% of the maximal inhibitory response possible for that agent; "i-Pr" refers to isopropyl; "kPa" refers to kilopascal or kilopascals; "kV" refers to kilovolts; "LAH" refers to lithium aluminum hydride; "LC-ES/MS" refers to Liquid Chromatography Electrospray Mass Spectrometry; "LDA" refers to lithium diisopropylamide; "mA" refers to milliamps or milliamperes; "mm" refers to minute or minutes; "Me" refers to methyl; "MeOH" refers to methanol or methyl alcohol; "MTBE" refers to methyl-tert-butyl ether; "n-BuLi" refers to n-butyllithium; "psi" refers to pounds per square inch; "rpm" refers to revolutions per minute; "RT" refers to room temperature; "SEM" refers to standard error of the mean; "SFC" refers to Supercritical Fluid Chromatography; "T3P" refers to 2,4,6-tripropyl-1,3,5,2,4,6-trioxatriphosphorinane-2,4,6-trioxide solution; "t-BuOH" refers to tert-butanol; "TEA" refers to triethylamine; "THF" refers to tetrahydrofuran; "t$_R$" refers to retention time; "U/mL" refers to units per milliliter.

It is understood by one of ordinary skill in the art that the terms "mesylate" and "methanesulfonic acid" each refer to the compound of the following structure:

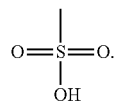

The compounds of the present invention, or salts thereof, may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. The following schemes, preparations, examples, and assays further illustrate the invention, but should not be construed to limit the scope of the invention in any way.

Scheme 1

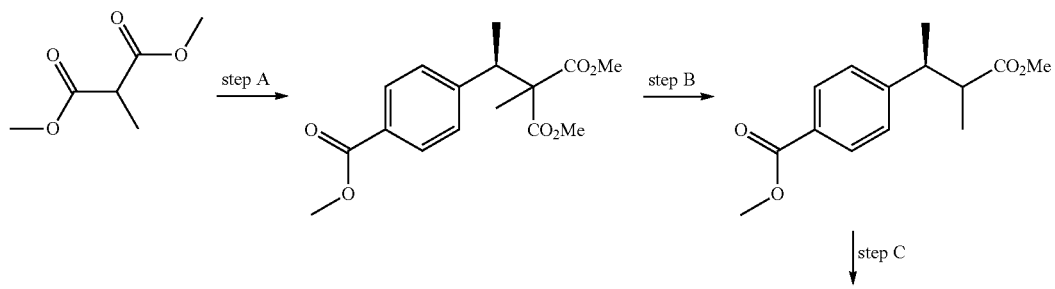

-continued

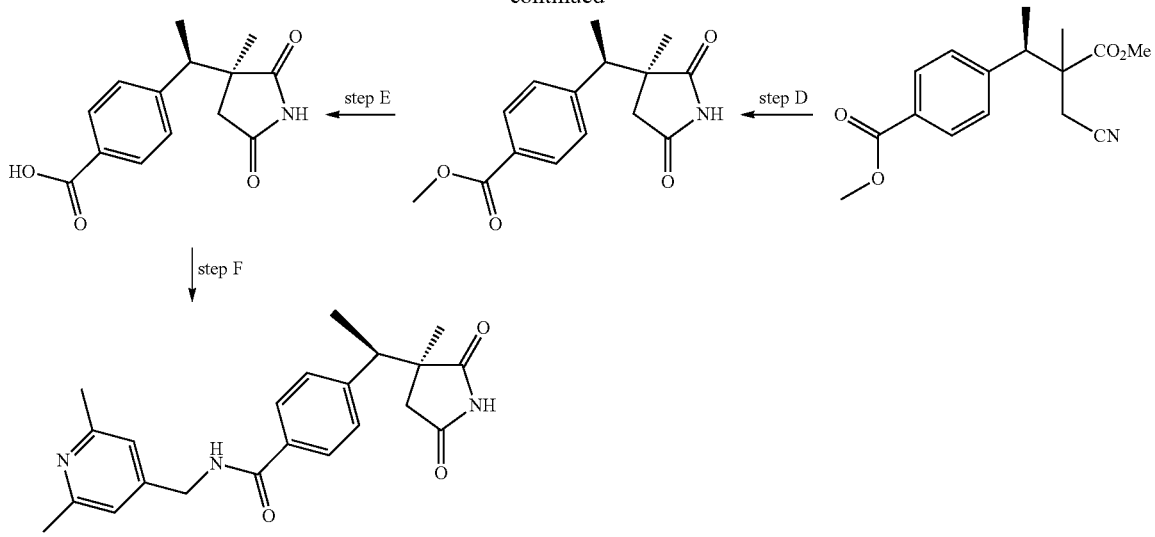

In Scheme 1, step A, about 1.1 equivalents of dimethyl 2-methylpropanedioate is combined with about 1 equivalent of methyl 4-{(1S)-1-[(methylsulfonyl)oxy]ethyl}benzoate in a suitable organic solvent, such as DMF under an inert atmosphere, such as nitrogen. The solution is cooled to about 0° C. and about 1.3 equivalents of a suitable inorganic base, which is relatively soluble in polar organic solvents, such as $Cs_2CO_3$, is added with stirring at about 0° C. for about 1 hr. The reaction is then gradually warmed to RT and the product is isolated and purified utilizing standard techniques well known in the art, such as extraction methods followed by chromatography. For example, the reaction mixture is treated with a suitable organic solvent, such as DCM and saturated aqueous sodium bicarbonate with mixing. The layers are separated, the aqueous layer is extracted with DCM, and the organic layers are combined, dried over anhydrous $Na_2SO_4$, filtered, and concentrated under reduced pressure to provide the crude product of step A. The crude product can then be purified by flash chromatography on silica, eluting with a suitable organic solvent mixture, such as hexanes/ethyl acetate to provide purified dimethyl {(1R)-1-[4-(methoxycarbonyl)phenyl]ethyl}(methyl)propanedioate of step A.

In Scheme 1, step B, the dimethyl {(1R)-1-[4-(methoxycarbonyl)phenyl]ethyl}(methyl)propanedioate is combined with a suitable wet organic solvent such as dimethylsulfoxide:water (about 43 mL:1 mL) under nitrogen at RT and about 1.3 equivalents of sodium chloride is added with stirring. The reaction is then heated to about 190° C. over about 50 mm and the reaction is then maintained at about 190° C. for about 3.5 hr. The reaction is then cooled to RT and the product is isolated and purified utilizing techniques well known in the art, such as extraction methods and chromatography. For example, the reaction is diluted with water and extracted with a suitable organic solvent, such as diethyl ether. The combined organic extracts are then washed with saturated aqueous sodium chloride, dried over anhydrous sodium sulfate, filtered, and concentrated under reduced pressure to provide the crude product of step B. This crude product can then be purified by flash chromatography on silica gel eluting with a suitable organic solvent mixture, such as hexanes/ethyl acetate to provide purified methyl 4-[(2S)-4-methoxy-3-methyl-4-oxobutan-2-yl]benzoate as a mixture of diastereomers.

In Scheme 1, step C, a solution of about 1.1 equivalents of a suitable organic base in a suitable organic solvent, such as lithium diisopropylamide (LDA) in hexane, is cooled to about −75° C. under an inert atmosphere, such as nitrogen. A solution of methyl 4-[(2S)-4-methoxy-3-methyl-4-oxobutan-2-yl]benzoate prepared in step B in a suitable organic solvent, such as tetrahydrofuran is added drop wise to the LDA solution over about 40 min. The reaction mixture is then stirred at about −75° C. for about 75 mm. A solution of about 1.5 equivalents of bromoacetonitrile in a suitable organic solvent, such as THF is added drop wise to the reaction mixture over about 12 mm. The reaction mixture is then allowed to slowly warm to RT and stirred for about 12 hr. The product is then isolated and purified utilizing techniques well known in the art, such as extraction methods and chromatography. For example, the reaction is quenched with saturated aqueous ammonium chloride and the reaction is extracted with a suitable organic solvent, such as ethyl acetate. The combined organic extracts are then washed with saturated aqueous sodium chloride, dried over anhydrous sodium sulfate, filtered, and concentrated under reduced pressure to provide the crude product of step C. The crude product is then purified by flash chromatography on silica gel eluting with a suitable organic solvent mixture, such as hexanes/ethyl acetate to provide methyl 4-[(2R)-3-(cyanomethyl)-4-methoxy-3-methyl-4-oxobutan-2-yl]benzoate as a mixture of diastereomers.

In Scheme 1, step D, neat methyl 4-[(2R)-3-(cyanomethyl)-4-methoxy-3-methyl-4-oxobutan-2-yl]benzoate prepared in step C is cooled in an ice/water bath and treated drop wise with about 10 equivalents of concentrated sulfuric acid over about 20 min. The cold bath is then removed and the reaction is stirred at RT for about 3 hr. The reaction mixture is then cooled in an ice/water bath, quenched with ice water, and the crude intermediate amide is isolated using standard extraction techniques. For example, the quenched reaction is extracted with a suitable organic solvent, such as DCM, the combined organic extracts are washed with water, dried over anhydrous sodium sulfate, filtered, and concentrated under reduced pressure to provide the crude intermediate amide. The crude intermediate is then dissolved in a suitable organic solvent, such as tetrahydrofuran and water, treated with about 2.5 equivalents of an inorganic base, such as sodium carbonate, and heated at about 50° C. for about 5 hr. The reaction mixture is then cooled in an ice/water bath, acidified to about pH~2 with 5 N aqueous HCl, and extracted with a suitable organic solvent, such as ethyl acetate. The combined organic extracts are washed with saturated aqueous sodium chloride, dried over anhydrous sodium sulfate, filtered, and concentrated under reduced pressure to give the crude product of step D. The crude product can then be purified by standard techniques well known in the art, such as flash chromatography on silica gel, eluting with a suitable organic eluent, such as hexanes/ethyl acetate to provide the purified product of step D, methyl 4-{(1R)-1-[(3S)-3-methyl-2,5-dioxopyrrolidin-3-yl]ethyl}benzoate, as the major diastereomer.

In Scheme 1, step E, about 3 equivalents of a suitable base, such as lithium hydroxide monohydrate is added to a solution of methyl 4-{(1R)-1-[(3S)-3-methyl-2,5-dioxopyrrolidin-3-yl]ethyl}benzoate in a mixture of suitable organic solvent, such as tetrahydrofuran and water. The reaction mixture is then stirred at about RT for about 16 hr, and then acidified to about pH~2 with a suitable acid, such as 1 N aqueous HCl. The organic solvent can then be removed under vacuum and the solid collected by filtration and dried under vacuum at about 45° C. to provide the product of step E, 4-{(1R)-1-[(3S)-3-methyl-2,5-dioxopyrrolidin-3-yl]ethyl}benzoic acid, which can be used in the next step without further purification.

In Scheme 1, step F, the product of step E, 4-{(1R)-1-[(3S)-3-methyl-2,5-dioxopyrrolidin-3-yl]ethyl}benzoic acid is coupled with 1-(2,6-dimethylpyridin-4-yl)methamine dihydrochloride utilizing standard amidation synthetic methods well known in the art. For example, the product of step E can be combined with about 1.2 equivalents of 1-(2,6-dimethylpyridin-4-yl)methamine dihydrochloride (Scheme 3, step B), about 1.2 equivalents of EDCI, and about 1.2 equivalents of HOBt in a suitable organic solvent, such as N,N-dimethylformamide About 4 equivalents of a suitable non-nucleophilic organic base, such as triethylamine is then added with stirring at RT. The reaction mixture is then stirred for about 16 hr and the product can then be isolated and purified utilizing techniques well known in the art, such as extraction methods and chromatography. For example, water can then be added to the reaction mixture which is then extracted with a suitable organic solvent, such as DCM. The organic extracts are combined, dried over anhydrous sodium sulfate, filtered, and concentrated under reduced pressure to provide the crude product of step F. The crude product can then be purified by flash chromatography on silica gel with a suitable eluent, such as DCM/methanol gradient to provide the purified product of step F, N-[(2,6-dimethylpyridin-4-yl)methyl]-4-{(1R)-1-[(3S)-3-methyl-2,5-dioxopyrrolidin-3-yl]ethyl}benzamide.

Alternatively, in Scheme 1, step F, the product of step E can be combined with about 1.05 equivalents of 1-(2,6-dimethylpyridin-4-yl)methamine dihydrochloride (Scheme 3, step B) in a suitable organic solvent such as DMF. The reaction mixture may be treated with about 6 equivalents DIPEA followed by a coupling agent such as BOP, with stirring at RT for about 1-2 hr and the product may be isolated utilizing techniques well known in the art, such as extraction methods and chromatography. For example, water can then be added to the reaction mixture which is then acidified to pH~7-8 with a suitable acid, such as 5 N HCl, and extracted with a suitable organic solvent, such as MTBE. The organic extracts are combined, dried over anhydrous sodium sulfate, filtered, concentrated under reduced pressure, and the crude product may be purified by chromatography on silica gel with a suitable eluent, such as a methanol/ethyl acetate in hexanes gradient, to obtain the purified product of step F, N-[(2,6-dimethylpyridin-4-yl)methyl]-4-{(1R)-1-[(3 S)-3-methyl-2,5-dioxopyrrolidin-3-yl]ethyl}benzamide.

Scheme 2

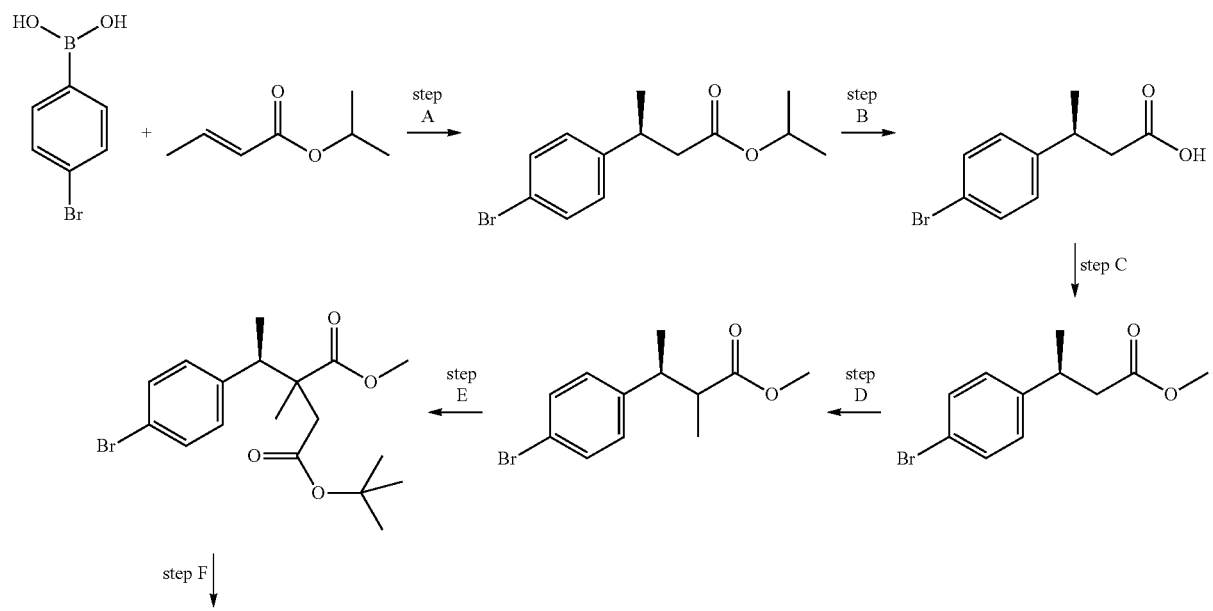

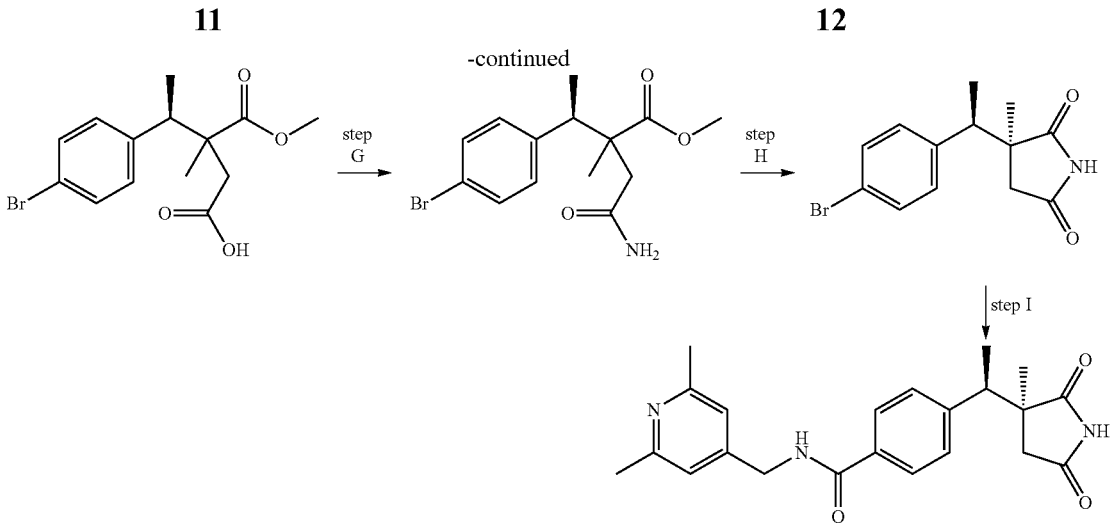

In Scheme 2, step A, asymmetric arylation of isopropyl (E)-but-2-enoate may be accomplished under coupling conditions using transition-metal catalysts such as rhodium with high enantioselectivity. rhodium catalysis product isopropyl (3S)-3-(4-bromophenyl)butanoate. For example, about 1.05-1.1 equivalents of 4-bromophenyl boronic acid may be treated with about 0.01 equivalents of a rhodium catalyst, specifically, bis(norbornadiene)rhodium(I) tetrafluoroborate, followed by addition of an appropriate chiral ligand such as 0.01-0.015 equivalents (R)-(+)-2,2'-bis(diphenylphosphino)-1,1'-binaphthyl, about 1 equivalent TEA, and about 1 equivalent of isopropyl (E)-but-2-enoate in an appropriate solvent mixture such as wet 1,4-dioxane or THF and water (about 8:1). The resulting reaction mixture may be heated to about 40° C. for about 18 hr. The product can then be isolated and purified utilizing techniques well known in the art, such as extraction methods and chromatography. For example, the reaction mixture may be diluted with water and extracted with an appropriate nonpolar organic solvent such as MTBE or DCM. The organic extracts may be combined, dried over anhydrous sodium sulfate, filtered, and concentrated under reduced pressure to provide the crude product of step A. The crude product may then be purified by flash chromatography on silica gel with a suitable eluent, such as hexanes/EtOAc gradient, to provide the purified product of step A, isopropyl (3S)-3-(4-bromophenyl)butanoate in high enantiomeric excess.

In Scheme 2, step B, hydrolysis of the product from Scheme 2, step A, may be accomplished under saponification conditions well known in the art. For example, (3S)-3-(4-bromophenyl)butanoic acid may be dissolved in an appropriate alcoholic solvent such as MeOH and treated with an excess of aqueous mineral base such as NaOH. After heating for about 1 hr, the product can then be isolated and purified utilizing techniques well known in the art, such as extraction, trituration, and evaporation methods. For example, the reaction mixture may be extracted with an appropriate organic solvent such as DCM and the resulting separated aqueous layer may be treated with an excess of a mineral acid such as conc. HCl to pH~4. The acidified aqueous layers may then be extracted with an appropriate organic solvent such as DCM. The organic extracts may be combined, dried over anhydrous sodium sulfate, filtered, and concentrated under reduced pressure to provide the crude product of step B. The crude product may be triturated with a non-polar organic solvent such as heptanes, the resulting precipitates may be filtered away, and the filtrate may be concentrated under reduced pressure to obtain the product of step B, (3S)-3-(4-bromophenyl)butanoic acid, in very high enantiomeric excess.

In Scheme 2, step C, esterification of the product from Scheme 2, step B, may be carried out under a wide range of acidic/basic esterification methods well known in the art, or by direct esterification with diazomethane. For example, (3S)-3-(4-bromophenyl)butanoic acid dissolved in an appropriate alcoholic solvent such as MeOH may be treated with an excess of a mineral acid, such as conc. $H_2SO_4$. The resulting mixture may be heated for about 2 hr, and the product can then be isolated by utilizing techniques well known in the art, such as extraction. The reaction mixture may be concentrated under reduced pressure, and the resulting residue may be partitioned between water and a suitable organic solvent such as MTBE. The organic extracts may be combined, washed with water, dried over anhydrous magnesium sulfate, filtered, and concentrated under reduced pressure to provide the product of step C, methyl (3S)-3-(4-bromophenyl)butanoate, suitable for use without additional purification.

In Scheme 2, step D, alkylation of the product of scheme 2, step C, may be achieved using variety of alkylation conditions well known in the literature. For example, methylation of methyl (3S)-3-(4-bromophenyl)butanoate may be accomplished by treatment with about 1.5-1.75 equivalents of a non-nucleophilic base such as n-butyllithium in an appropriate solvent such as anhydrous THF at low temperature followed by quenching of the resulting anion with about 1.5-1.6 equivalents methyl iodide. The product can then be isolated by utilizing techniques well known in the art, such as extraction. The reaction mixture may be partitioned between water and an appropriate organic solvent such as MTBE. The combined organic extracts may be washed sequentially with water, saturated aqueous NaCl, dried over magnesium sulfate, filtered and concentrated under reduced pressure to obtain the product of step D, (3S,2R/S)-methyl 3-(4-bromophenyl)-2-methylbutanoate, as a mixture of diastereomers suitable for use without additional purification.

In Scheme 2, step E, the product of Scheme 2, step D, (3S,2R/S)-methyl 3-(4-bromophenyl)-2-methylbutanoate as a mixture of diastereomers, may be treated with about 1 equivalent of a strong organic base such as n-butyllithium in an appropriate organic solvent such as anhydrous THF at low temperature. The resulting mixture may then be treated with a solution of about 0.9 equivalents tert-butyl 2-bromoacetate. The product can then be isolated by utilizing techniques well known in the art, such as extraction. The reaction mixture may be partitioned between water and an appropriate organic solvent such as MTBE, and the combined organic extracts may be washed sequentially with water and saturated aqueous NaCl. The organic extracts may be dried over magnesium sulfate, filtered, and concentrated under reduced pressure to obtain the product of step E, 4-(tert-butyl) 1-methyl (S/R)-2-((R)-1-(4-bromophenyl) ethyl)-2-methylsuccinate, as a mixture of diastereomers suitable for use without additional purification.

In Scheme 2, step F, a mixture of the diastereomeric esters from the product of Scheme 2, step E, may be hydrolyzed under conditions well known in the prior art. For example, 4-(tert-butyl) 1-methyl (S/R)-2-((R)-1-(4-bromophenyl) ethyl)-2-methylsuccinate may be dissolved in an appropriate organic solvent such as DCM and treated with an excess or an organic acid such as TFA. The resulting mixture may be stirred at RT for about 18 hr, and the product can then be isolated by utilizing techniques well known in the art, such as extraction. The reaction mixture may be washed sequentially with water and saturated aqueous NaCl, the organic extracts may be dried over magnesium sulfate, filtered and concentrated under reduced pressure to obtain the product of step F, (3S/R,4R)-4-(4-bromophenyl)-3-(methoxycarbonyl)-3-methylpentanoic acid, as a mixture of diastereomers suitable for use without additional purification.

In Scheme 2, step G, a mixture of the diastereomers from Scheme 2, step F, (3S/R,4R)-4-(4-bromophenyl)-3-(methoxycarbonyl)-3-methylpentanoic acid, maybe dissolved in an appropriate polar organic solvent such as anhydrous DMF and treated sequentially with a non-nucleophilic base such as about 3 equivalents of TEA or DIPEA, about 1.2 equivalents of an amide coupling reagent such as HATU, and a solution of excess methanolic ammonia. The resulting mixture may be stirred at RT for about 2-12 hr, and the product can then be isolated by utilizing techniques well known in the art, such as extraction. The reaction mixture may be partitioned between water and an appropriate organic solvent such as DCM, the layers may be separated, and the combined organic extracts are washed sequentially with water and saturated aqueous NaCl. The extracts may then be dried over magnesium sulfate, filtered, and concentrated under reduced pressure to obtain the product of step G, methyl (2S/R)-4-amino-2-[(1R)-1-(4-bromophenyl) ethyl]-2-methyl-4-oxo-butanoate, as a mixture of diastereomers suitable for use without additional purification.

In Scheme 2, step H, a mixture of the diastereomeric product of Scheme 2, step G may be cyclized by heating in the presence of a non-nucleophilic base followed by separation of diastereomers under chiral chromatography conditions. For example, methyl (2S/R)-4-amino-2-[(1R)-1-(4-bromophenyl)ethyl]-2-methyl-4-oxo-butanoate may be dissolved in a mixture of THF/water (about 1:1), treated with about 2.5 equivalents of a non-nucleophilic base such as sodium carbonate, and the resulting mixture may be heated to about 60° C. for about 2 hr. The product can then be isolated by utilizing techniques well known in the art, such as extraction followed by separation of the diastereomers under chiral chromatography conditions. For example, the reaction mixture is extracted with EtOAc, the combined organic extracts are dried over magnesium sulfate, filtered, and concentrated under reduced pressure to give a crude mixture of diastereomers. The diastereomers may be separated by chiral SFC technology, using an isocratic solvent system of EtOH containing a small amount of a non-nucleophilic amine such as N,N-diethylmethylamine/CO$_2$ (about 1:9) to obtain the separated products of step H, (3S)-3-[(1R)-1-(4-bromophenyl)ethyl]-3-methyl-pyrrolidine-2,5-dione and (3R)-3-[(1R)-1-(4-bromophenyl)ethyl]-3-methyl-pyrrolidine-2,5-dione.

In Scheme 2, step I, the product of step H may be carbonylated with in situ amidation under conditions well described in the art. For example, (3S)-3-[(1R)-1-(4-bromophenyl)ethyl]-3-methyl-pyrrolidine-2,5-dione, about 1.2 equivalents (2,6-dimethyl-4-pyridyl)methanaminedihydrochloride (Scheme 3, step B), about 0.033 equivalents of a transitional-metal reagent such as palladium(II) acetate, about 0.064 equivalents of a suitable ligand reagent such as 4,5-bis(diphenylphosphino)-9,9-dimethylxanthene, and about 3.5 equivalents of a non-nucleophilic base such as DIPEA may be slurried in a non-polar organic solvent such as toluene in a sealed reaction vessel pressurized to about 60 psi under an atmosphere of carbon monoxide. The resulting mixture may be heated for about 12-18 hr at 100° C., then cooled to RT, filtered over a bed of diatomaceous earth, and concentrated under reduced pressure. The product may then be isolated by utilizing techniques well known in the art, such as precipitation and filtration. For example, the crude residue obtained after solvent evaporation may be diluted with water and an appropriate organic solvent such as DCM (1:1 mixture), and the resulting solid may be collected by filtration and triturated with diethyl ether to give the product of step I, N-[(2,6-dimethylpyridin-4-yl)methyl]-4-{(1R)-1-[(3S)-3-methyl-2,5-dioxopyrrolidin-3-yl]ethyl}benzamide.

Scheme 3

In Scheme 3, step A, about 1.0-1.2 equivalents to Zn(CN)$_2$ may be added to a solution of 4-bromo-2,6-dimethylpyridine in a suitable polar organic solvent such as DMF containing about 5-10 mol % of a suitable transition-metal catalyst/ligand complex, such as tetrakis(triphenylphosphine)palladium (0). After heating for about 5-18 hr, the reaction mixture may be cooled to RT, and the product may be isolated and purified utilizing standard techniques well known in the art, such as extraction methods followed by solvent evaporation or by chromatography. For example, the reaction mixture is treated with a suitable organic solvent, such as EtOAc, and aqueous NH$_4$OH with mixing. The layers are separated, the aqueous layer is extracted with EtOAc, and the organic layers are combined, dried over anhydrous Na$_2$SO$_4$, filtered, and concentrated under reduced pressure to provide the crude product of step A. The crude product can then be purified by flash chromatography on silica, eluting with a suitable organic solvent mixture, such as hexanes/ethyl acetate, to provide the product, 4-cyano-2,6-dimethylpyridine, of step A. Alternately, the crude reaction mixture may be diluted with a suitable organic solvent, such as MTBE, followed by a basic (pH~10) aqueous solution, such as 30% NH$_4$OH, the layers are separated, the aqueous phase is additionally extracted with MTBE, and the combined organic extracts are washed with 10% NH$_4$OH, dried over anhydrous Na$_2$SO$_4$, filtered, and concentrated under reduced pressure to provide the product of step A, 4-cyano-2,6-dimethylpyridine, suitable for use without additional purification.

In Scheme 3, step B, the product 4-cyano-2,6-dimethylpyridine of step A may be reduced under a variety of methods well known in the art, such as chemical hydride reduction with a reducing agent such as $LiBH_4$ or $NaBH_4$ or by hydrogenation with a transition-metal such as $Pd(OH)_2$ or Pd on carbon. Additionally, hydrogenation may be performed in the presence of a mineral acid in water or in a suitable organic solvent, such as THF or DMF, to provide the reduced product as the HCl salt For example, 4-cyano-2,6-dimethylpyridine, product of step A, is dissolved in a suitable organic solvent such as MeOH or EtOH, in the presence of excess HCl either in water or in 1,4-dioxane, and the solution is treated with excess 5-10% Pd/C. The reaction mixture is subjected to hydrogenation under pressure at about 60 psi at RT overnight. The mixture is filtered, and the filtrate is concentrated to give the crude product of step B. Subsequent precipitation of the product of step B may be achieved by methods well known to those skilled in the art, such as trituration, crystallization, or recrystallization. For example, the crude product of step B may be treated with a mixture of boiling EtOH/EtOAc until dissolution; subsequent cooling with crystallization and collection of the product by filtration may give the product 1-(2,6-dimethyl-pyridin-4-yl)methamine dihydrochloride of Step B. Alternately, the crude product may be suspended in a mixture of MeOH/MTBE, with collection of the resulting solid, 1-(2,6-dimethylpyridin-4-yl)methamine dihydrochloride, product of step B, by filtration.

Scheme 4

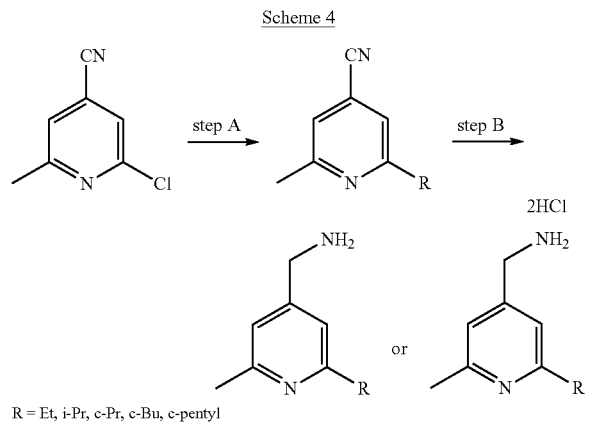

R = Et, i-Pr, c-Pr, c-Bu, c-pentyl

Scheme 4 depicts the preparation of 2-substituted-6-methyl-pyridylmethanamines. In Scheme 4, step A, a person of ordinary skill in the art may appreciate the conversion of a 2-chloropyridine to a 2-alkylpyridine using Grignard, alkyllithium, alkylboronate or alkylzinc reagent. For example, treatment of about 3.0-3.6 equivalents 2-chloro-6-methylisonicotinonitrile (Bioorganic & Medicinal Chemistry Letters, 20(2), 576-580; 2010) with about 1.0-1.5 equivalents of an appropriately substituted Grignard, alkylboronate or alkylzinc reagent in a suitable polar solvent, such as NMP or 1,4-dioxane, or in a biphasic mixture of a suitable organic solvent such as toluene, benzene, or DMF containing water, in the presence of about 0.1-0.2 equivalents of a transition metal catalyst, for example iron (III) acetoacetate (R=Et), $Pd(OAc)_2$ in the presence of a suitable phosphine ligand such as tricyclohexylphosphine tetrafluoroborate, or [1,1'-bis(diphenylphosphino)-ferrocene]dichloropalladium(II) (R=i-Pr, c-Pr, c-Bu, c-pentyl) from about room temperature to about 120° C., gives the crude 2-alkyl product of Scheme 4, step A, which may be isolated and purified under conditions well known in the art, such as extraction and chromatography. For example, the reaction is diluted with water and filtered over a bed of diatomaceous earth, and the filtrate is extracted with an appropriate organic solvent such as EtOAc or DCM. The organic extract is dried over $Na_2SO_4$, filtered, concentrated under reduced pressure, and purified by flash chromatography on silica gel using hexanes or heptanes/EtOAc, to obtain the desired 2-alkyl-6-methyl-4-pyridinecarbonitrile, product of Scheme 4, step A. The carbonitrile moiety may be reduced to the methylamine under an array of conditions well appreciated in the art. For example, the desired 2-alkyl-6-methyl-4-pyridinecarbonitrile, about 1 equivalent of the product of Scheme 4, step A, may be treated with excess Raney nickel under an atmosphere of hydrogen at 20-60 psi in a suitable polar solvent mixture, such as $NH_3$ in MeOH. The reaction mixture may be filtered, concentrated, and the resulting residue triturated sequentially with an appropriate mixture of organic solvents, such as toluene, ACN, MeOH/toluene, and ACN/toluene, with subsequent filtration, to obtain the appropriately substituted (2-methyl-6-methyl-4-pyridyl)methanamine as the dihydrochloride salt. Alternatively, the resulting crude product may be isolated and purified under conditions well known in the art, such as extraction and chromatography methods, to obtain the appropriately substituted (2-methyl-6-methyl-4-pyridyl)methanamine as the free base.

Scheme 5

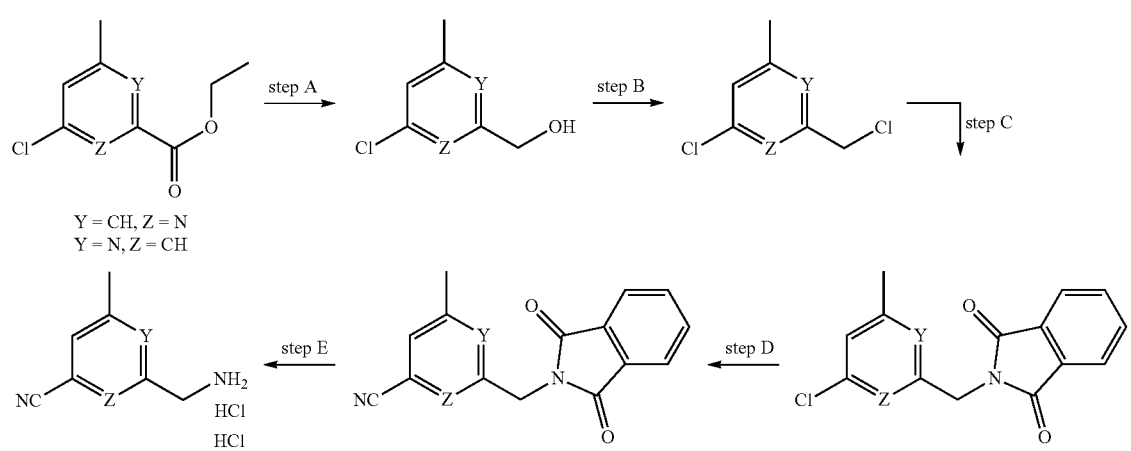

Y = CH, Z = N
Y = N, Z = CH

Scheme 5 depicts the preparation of 6-(aminomethyl)-4-methyl-pyridine-2-carbonitrile dihydrochloride. In Scheme 5, step A, reduction of ethyl 2-pyridine-carboxylates may be accomplished under a wide array of methods well described in the art. For example, about 1 equivalent of ethyl 6-chloro-4-methylpyridine-2-carboxylate (Y=CH, Z=N) is treated with about 1.7 equivalents of sodium borohydride in EtOH at RT to obtain (6-chloro-4-methyl-2-pyridyl)nethanol, the product of Scheme 5, step A (Y=CH, Z=N), suitable for use without additional purification. Halogenation to the alkyl halide may be recognized by one of ordinary skill under various halogenation conditions. For example, about 1 equivalent of the product of Scheme 5, step A, (6-chloro-4-methyl-2-pyridyl)nethanol (Y=CH, Z=N) is treated with about 2 equivalents of thionyl chloride in a suitable organic solvent such as DCM of CHCl₃ from about RT to reflux, and evaporation of the solvents may yield the desired 2-chloro-6-(chloromethyl)-4-methyl-pyridine, the product of Scheme 5, step B (Y=CH, Z=N), suitable for use without additional purification. The product of Scheme 5, step B, 2-chloro-6-(chloromethyl)-4-methyl-pyridine (Y=CH, Z=N), may be treated with a variety of protected amines suitable to withstand additional functionalization. For example, about 1 equivalent of potassium phthalimide may be treated with 2-chloro-6-(chloromethyl)-4-methyl-pyridine, the product of Scheme 5, step B (Y=CH, Z=N), in a suitable polar solvent such as DMF. Subsequent dilution with water may yield the solid product of Scheme 5, step C (Y=CH, Z=N), 2-[(6-chloro-4-methyl-2-pyridyl)methyl]isoindoline-1,3-dione, which may be isolated by methods well known in the art, such as filtration. The chloro moiety of 2-[(6-chloro-4-methyl-2-pyridyl)methyl]isoindoline-1,3-dione, product of Scheme 5, step C (Y=CH, Z=N), may be displaced with a wide of nucleophiles as well described in the literature, such as by SNAR reaction or by transition metal-mediated processes. For example, about 1 equivalent of the product of Scheme 5, step C (Y=CH, Z=N), 2-[(6-chloro-4-methyl-2-pyridyl)methyl]isoindoline-1,3-dione, may be treated with about 0.75 equivalents of zinc cyanide in the presence of about 0.05 equivalents of [1,1'-bis(diphenylphosphino)ferrocene]palladium(II) dichloride and about 0.25 equivalents of elemental zinc in a suitable polar organic solvent such as DMF or DMSO with heating from 100-140° C. A person skilled in the art will recognize that the product of this transformation may be isolated and purified by standard techniques well known in the art, such as extraction and chromatography. For example, the cooled reaction mixture may be diluted with water and extracted with a suitable solvent such as DCM or EtOAc, washed sequentially with NH₄OH and saturated aqueous NaCl, and the organic extract may be dried over Na₂SO₄ or MgSO₄. The resulting crude product may be subjected to flash chromatography on silica eluting with a suitable organic solvent mixture, such as hexanes/ethyl acetate, to provide the product, 6-[(1,3-dioxoisoindolin-2-yl)methyl]-4-methyl-pyridine-2-carbonitrile, of Scheme 5, step D (Y=CH, Z=N). Removal of the amine protecting group may be accomplished by one of ordinary skill in the art. For example, treatment of about 1 equivalent of 6-[(1,3-dioxoisoindolin-2-yl)methyl]-4-methyl-pyridine-2-carbonitrile, the product of Scheme 5, step D (Y=CH, Z=N), with about 2 equivalents of hydrazine hydrate in a suitable polar organic solvent such as EtOH under reflux, may yield the crude deprotected amine upon solvent evaporation. Subsequent isolation and purification of the crude amine may be accomplished by standard techniques known in the art, such as selective cation exchange and salt preparation. For example, the crude amine may be passed through an SCX column, eluting with a mixture of NH₃/MeOH; the methanolic ammonia fractions may be evaporated, the resulting residue redissolved in MeOH, and the resulting solution treated with 2-10 equivalents of HCl in a suitable organic solvent, such as Et₂O or 1,4-dioxane, to obtain the solid 6-(aminomethyl)-4-methyl-pyridine-2-carbonitrile dihydrochloride after collection by filtration. The syntheses of compounds where Y=N and Z=CH may be performed via analogous methods.

Scheme 6

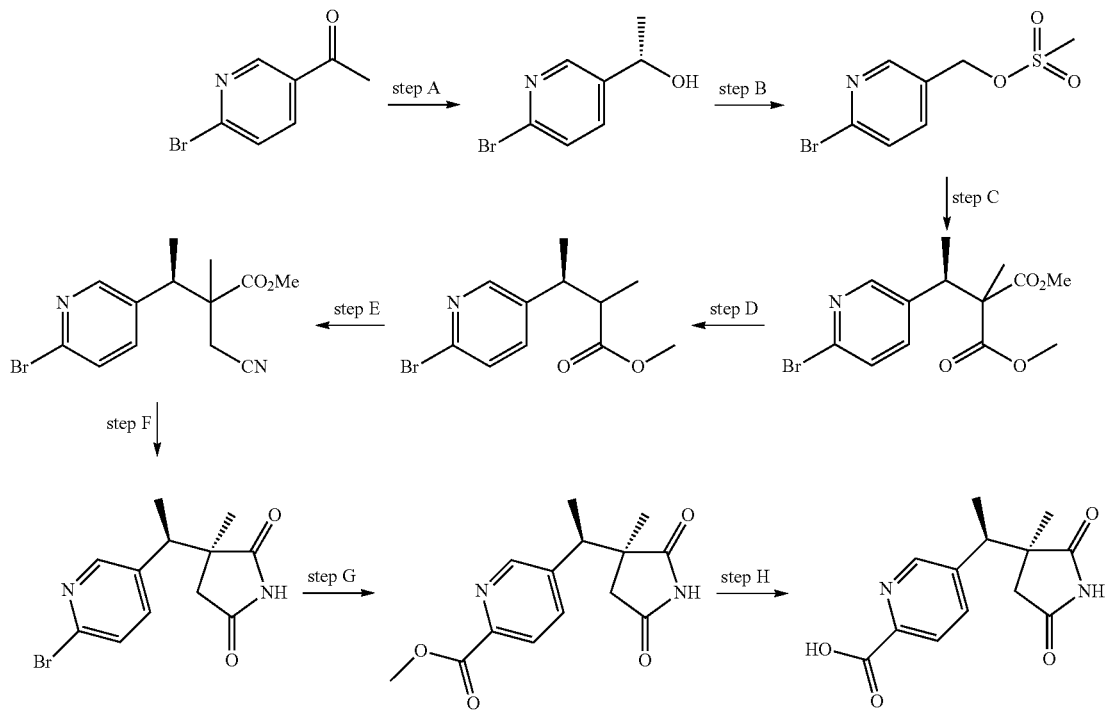

Scheme 6 depicts the synthesis of 5-[(1R)-1-[(3S)-3-methyl-2,5-dioxo-pyrrolidin-3-yl]ethyl]pyridine-2-carboxylic acid. In Scheme 2, step A, 1-(6-bromopyridin-3-yl)ethanone may be reduced stereoselectively by hydrogenation in the presence of an array of transition metal catalysts. For example, about 1 equivalent 1-(6-bromopyridin-3-yl)ethanone in a suitable polar solvent, such as EtOH: 2-propanol (about 1.2 mL: 1 mL) is treated with about 0.00075 equivalents chloro{(R)-(+)-2,2'-bis[di(3,5-xylyl)phosphino]-1,1'-binaphthyl)}[(2R)-(−)-1-(4-methoxyphenyl)-1-(4-methoxyphenyl-kC)-3-methyl-1,2-butanediamine]ruthenium(II) [(R)-RUCY™-XylBINAP] and about 0.0075 equivalents KO$^t$Bu in an appropriately sealed and evacuated hydrogenation vessel. The system is then filled with hydrogen and stirred at about RT for about 6 hr. The crude product is isolated and purified utilizing standard techniques well known in the art, such as filtration, solvent removal and chromatography. For example, the reaction mixture is filtered, evaporated under reduced pressure to provide the crude product of step A. The crude product can then be purified by flash chromatography on silica, eluting with a suitable organic solvent mixture, such as DCM/MTBE, to provide (1S)-1-(6-bromopyridin-3-yl)ethanol of Scheme 6, step A.

In Scheme 6, step B, the product of Scheme 6, step A, (1S)-1-(6-bromopyridin-3-yl)ethanol, is dissolved in a suitable organic solvent such as DCM and treated with about 1.3 equivalents of a suitable organic, non-nucleophilic base such as TEA at about 0° C. About 1.2 equivalents of a suitable sulfonylating reagent, such as methanesulfonyl chloride, are added, and the product is isolated and purified utilizing standard techniques well known in the art, such as extraction. For example, the reaction mixture is treated with water, and the layers are separated; the aqueous layer is extracted twice with DCM, the organic layers are combined, washed with saturated aqueous NaHCO$_3$, dried over anhydrous Na$_2$SO$_4$, filtered, and concentrated under reduced pressure to provide (1S)-1-(6-bromopyridin-3-yl)ethyl methanesulfonate of Scheme 6, step B, which can be used in the next step without additional purification.

Scheme 6, steps C-H, are performed under analogous conditions to those described in Scheme 1, steps A-F, to obtain the requisite 5-[(1R)-1-[(3S)-3-methyl-2,5-dioxopyrrolidin-3-yl]ethyl]pyridine-2-carboxylic acid.

Scheme 7

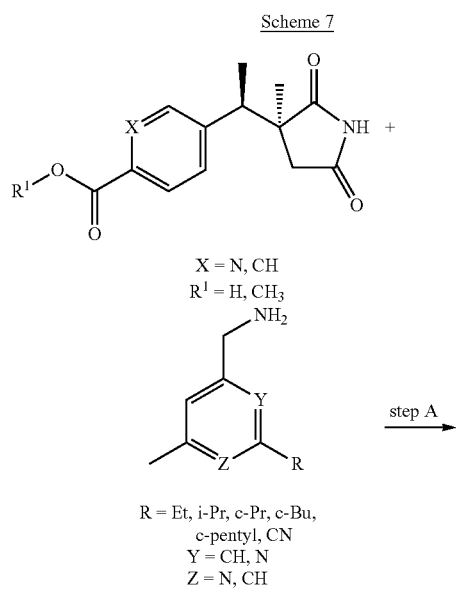

X = N, CH
R$^1$ = H, CH$_3$

R = Et, i-Pr, c-Pr, c-Bu, c-pentyl, CN
Y = CH, N
Z = N, CH step A

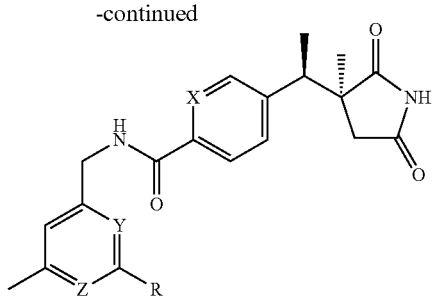

Scheme 7 depicts the preparation of succinimide carboxamide compounds, wherein the appropriate carboxylic acid may be coupled to an appropriate pyridylamine or pyridylaine dihydrochloride under an array of amide coupling conditions well known in the art. For example, the amide coupling reaction may be performed analogously to that depicted in Scheme 1, step F, or may be performed with such coupling agents as HOBt, HOAT, HATU, or T3P, among many others well described in the literature. Alternatively, the amide coupling may be performed on the carboxylic ester (R$^1$=CH$_3$) under a variety of conditions well known in the art, including, but not limited to, heating a mixture of the appropriate carboxylic ester and an appropriate pyridylamine or pyridylamine salt (e.g., dihydrochloride) at a temperature of about 150-170° C. in a sealed vessel in a suitable non-polar organic solvent such as toluene or xylene.

PREPARATIONS AND EXAMPLES

The following Preparations and Examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

The R- or S-configuration of the compound of the invention may be determined by standard techniques such as X-ray analysis and correlation with chiral-HPLC retention time.

LC-ES/MS is performed on an AGILENT® HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX® GEMINI® NX C18 2.1×50 mm 3.0 µm; gradient: 5-100% B in 3 min, then 100% B for 0.75 min column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: XTERRA® MS C18 columns 2.1×50 mm, 3.5 µm; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min; column temperature: 50° C.+/−10° C.; flow rate: 1.2 mL/min; Solvent A: 10 mM NH$_4$HCO$_3$ pH 9; Solvent B: ACN; wavelength: 214 nm.

Preparative reversed phase chromatography is performed on an AGILENT® 1200 LC-ES/MS equipped with a Mass Selective Detector mass spectrometer and a LEAP® autosampler/fraction collector. High pH methods are run on a 75×30 mm PHENOMENEX® GEMINI®-NX, 5μ particle size column with a 10×20 mm guard. Flow rate of 85 mL/min. Eluent is 10 mM ammonium bicarbonate (pH 10) in acetonitrile.

NMR spectra are performed on a Bruker AVIII HD 400 MHz NMR Spectrometer, obtained as CDCl$_3$ or (CD$_3$)$_2$SO solutions reported in ppm, using residual solvent [CDCl$_3$, 7.26 ppm; (CD$_3$)$_2$SO, 2.05 ppm] as reference standard. When peak multiplicities are reported, the following abbreviations may be used: s (singlet), d (doublet), t (triplet), q (quartet), m (multiplet), br-s (broad singlet), dd (doublet of doublets), dt (doublet of triplets). Coupling constants (J), when reported, are reported in hertz (Hz).

Preparation 1

Dimethyl {(1R)-1-[4-(methoxycarbonyl)phenyl]ethyl}(methyl)propanedioate

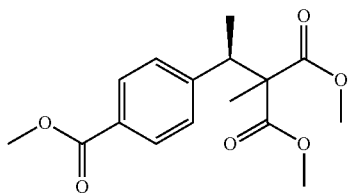

Scheme 1, step A: To a stirred solution of dimethyl 2-methylpropanedioate (12.2 g, 82.9 mmol) and methyl 4-{(1S)-1-[(methylsulfonyl)oxy]ethyl}benzoate (21.8 g, 75.4 mmol) in DMF (150 mL) under nitrogen at 0° C. is added Cs$_2$CO$_3$ (32.2 g, 98.0 mmol). The reaction mixture is thoroughly purged with nitrogen, stirred at 0° C. for 1 hr, and gradually warmed to ambient temperature. DCM and saturated aqueous NaHCO$_3$ are added and the layers are separated. The aqueous layer is extracted twice with DCM. The organic layers are combined, dried over Na$_2$SO$_4$, filtered, and concentrated under reduced pressure to give a yellow oil. The crude product is purified by flash chromatography on silica, eluting with hexanes/ethyl acetate (gradient from 49:1 to 7:3). The pure chromatography fractions are combined and concentrated under reduced pressure to give the title compound (22.62 g, 93%). LC-ES/MS (m/z): 309.0 (M+H). $^1$H NMR (CDCl$_3$) δ 1.37 (s, 3H), 1.39 (d, J=7.1 Hz, 3H), 3.59 (s, 3H), 3.74 (s, 3H), 3.74 (q, J=7.1 Hz, 1H), 3.89 (s, 3H), 7.25-7.30 (m, 2H), 7.91-7.96 (m, 2H).

Preparation 2

Methyl 4-[(2S)-4-methoxy-3-methyl-4-oxobutan-2-yl]benzoate

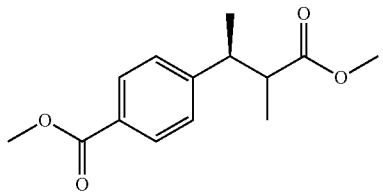

Scheme 1, step B: To a stirred solution of dimethyl {(1R)-1-[4-(methoxycarbonyl)phenyl]ethyl}(methyl)propanedioate (22.6 g, 73.7 mmol) in dimethylsulfoxide (200 mL)/water (4.67 mL) under nitrogen at RT is added NaCl (5.58 g, 95.4 mmol). The reaction flask is placed in an oil bath and heated to 190° C. over 50 min and the resulting reaction is maintained at 190° C. for 3.5 hr, at which time TLC (30% EtOAc/Hexane) showed disappearance of starting material. After cooling to RT, the reaction is diluted with water (400 mL) and extracted with Et$_2$O (3×150 mL). The extract is washed with saturated aqueous NaCl, dried over Na$_2$SO$_4$, filtered, and concentrated under reduced pressure to give a brown oil. The crude product is purified by flash chromatography on silica, eluting with hexanes/ethyl acetate (gradient from 19:1 to 4:1). The pure chromatography fractions are combined and concentrated under reduced pressure to give the title compound (13.35 g, 72%) as a mixture of diastereomers. LC-ES/MS (m/z): 251.0 (M+H).

Preparation 3

Methyl 4-[(2R)-3-(cyanomethyl)-4-methoxy-3-methyl-4-oxobutan-2-yl]benzoate

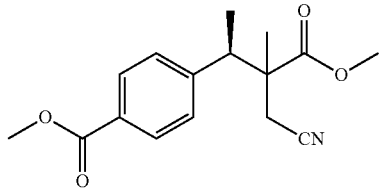

Scheme 1, step C: A solution of LDA [freshly prepared from diisopropyl amine (11.3 mL, 80.4 mmol) and n-butyllithium (2.5 M in hexane, 32.2 mL, 80.4 mmol)] is cooled to −75° C. under nitrogen. A solution of methyl 4-[(2S)-4-methoxy-3-methyl-4-oxobutan-2-yl]benzoate (18.3 g, 73.1 mmol) in THF (50 mL) is added drop wise to the LDA solution over 40 min. The reaction mixture is aged at −75° C. for 75 min before adding a solution of bromoacetonitrile (7.87 mL, 110 mmol)/THF (20 mL) drop wise, over 12 min. The reaction mixture is allowed to slowly warm to RT and stirred overnight. After quenching with saturated aqueous NH$_4$Cl, the reaction is extracted with EtOAc (3×100 mL). The extract is washed with saturated aqueous NaCl, dried over Na$_2$SO$_4$, filtered, and concentrated under reduced pressure to give a dark oil. The crude product is purified by flash chromatography on silica, eluting with hexanes/ethyl acetate (gradient from 19:1 to 3:2). The pure chromatography fractions are combined and concentrated under reduced pressure to give the title compound (12.08 g, 57%) as a mixture of diastereomers. LC-ES/MS (m/z): 307.0 (M+NH$_4$$^+$).

Preparation 4

Methyl 4-{(1R)-1-[(3S)-3-methyl-2,5-dioxopyrrolidin-3-yl]ethyl}benzoate (Major Diastereomer) And Methyl 4-{(1R)-1-[(3R)-3-methyl-2,5-dioxopyrrolidin-3-yl]ethyl}benzoate (Minor Diastereomer)

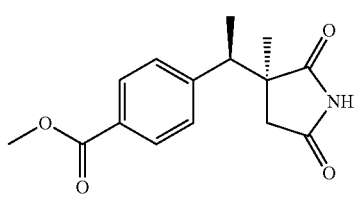

Major diastereomer

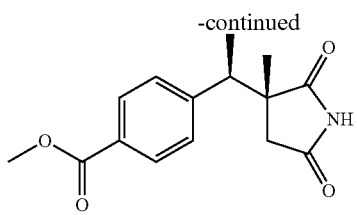

Minor diastereomer

Scheme 1, step D: Neat methyl 4-[(2R)-3-(cyanomethyl)-4-methoxy-3-methyl-4-oxobutan-2-yl]benzoate (33.4 g, 115 mmol) is cooled in an ice/water bath and treated drop wise with concentrated $H_2SO_4$ (66.8 mL, 1180 mmol) over a 20 min period. The cold bath is removed and the reaction is stirred at RT for 3 hr. The reaction mixture is then cooled in an ice/water bath, quenched with ice water (400 mL), and extracted with DCM (2×250 mL). The extract is washed with water, dried over $Na_2SO_4$, filtered, and concentrated under reduced pressure to give the crude intermediate amide as a yellow foam. The crude intermediate is dissolved in THF (200 mL) and water (200 mL), treated with $Na_2CO_3$ (30.7 g, 289 mmol), and heated at 50° C. for 5 hr. After cooling in an ice/water bath, the reaction mixture is acidified to pH~2 with 5 N aqueous HCl and extracted with EtOAc (2×150 mL). The extract is washed with saturated aqueous NaCl, dried over $Na_2SO_4$, filtered, and concentrated under reduced pressure to give a yellow foam. The crude product is purified by flash chromatography on silica, eluting with hexanes/ethyl acetate (gradient from 9:1 to 1:1). The pure chromatography fractions are combined and concentrated under reduced pressure to give the major diastereomer as the first eluting material, methyl 4-{(1R)-1-[(3S)-3-methyl-2,5-dioxopyrrolidin-3-yl]ethyl}benzoate, (17.23 g, 54%) and the minor diastereomer as the second eluting material, methyl 4-{(1R)-1-[(3R)-3-methyl-2,5-dioxopyrrolidin-3-yl]ethyl}benzoate, (5.01 g, 16%).

Major isomer: $^1$H NMR (CDCl$_3$): δ 1.23 (s, 3H), 1.35 (d, J=7.1 Hz, 3H), 2.22 (d, J=18.4 Hz, 1H), 3.01 (d, J=18.4 Hz, 1H), 3.24 (q, J=7.1 Hz, 1H), 3.92 (s, 3H), 7.24-7.29 (m, 2H), 7.86 (br s, 1H), 7.97-8.02 (m, 2H).

Minor isomer: $^1$H NMR (CDCl$_3$): δ 1.38 (d, J=7.2 Hz, 3H), 1.44 (s, 3H), 2.35 (d, J=18.5 Hz, 1H), 2.83 (d, J=18.5 Hz, 1H), 3.33 (q, J=7.2 Hz, 1H), 3.90 (s, 3H), 7.25-7.30 (m, 2H), 7.46 (br s, 1H), 7.92-7.97 (m, 2H).

Preparation 5

4-{(1R)-1-[(3S)-3-methyl-2,5-dioxopyrrolidin-3-yl]ethyl}benzoic acid

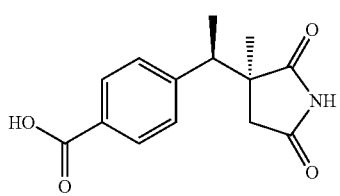 [SMILES: C[C@H](c1ccc(C(=O)O)cc1)[C@]1(C)CC(=O)NC1=O]

Scheme 1, step E: Lithium hydroxide monohydrate (3.16 g, 75.3 mmol) is added to a solution of methyl 4-{(1R)-1-[(3S)-3-methyl-2,5-dioxopyrrolidin-3-yl]ethyl}benzoate (6.91 g, 25.1 mmol) dissolved in THF (84 mL) and water (36 mL). After stirring at RT for 16 hr, the reaction mixture is acidified to pH~2 with 1 N aqueous HCl and the THF removed in vacuo. The resulting solid is collected by filtration and dried in a vacuum oven at 45° C. to give the title compound (5.96 g, 91%). $^1$H NMR (DMSO-d$_6$): δ 1.06 (s, 3H), 1.22 (d, J=7.1 Hz, 3H), 2.16 (d, J=18.2 Hz, 1H), 3.02 (d, J=18.2 Hz, 1H), 3.12 (q, J=7.1 Hz, 1H), 7.39-7.45 (m, 2H), 7.84-7.89 (m, 2H), 11.22 (s, 1H), 12.85 (br s, 1H).

Preparation 6

Isopropyl (3S)-3-(4-bromophenyl)butanoate

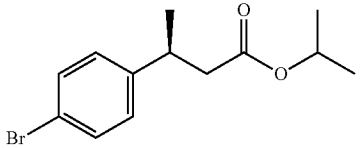 [SMILES: CC(C)OC(=O)C[C@H](C)c1ccc(Br)cc1]

Scheme 2, step A: To a deoxygenated solution of (4-bromophenyl)boronic acid (110 g, 547.73 mmol) in 1,4-dioxane (750 mL) under $N_2$ atmosphere is added bis(norbornadiene)rhodium(I) tetrafluoroborate (2 g, 5.13 mmol) followed by (R)-(+)-2,2'-bis(diphenylphosphino)-1,1'-binaphthyl (4.5 g, 7.2 mmol). The mixture is aged at room temperature for 1 hr before adding H$_2$O (100 mL), TEA (70 mL, 502 mmol), and isopropyl (E)-but-2-enoate (65 g, 507.14 mmol). The resulting red solution is heated to 40° C. for 18 hr. The reaction mixture is concentrated under reduced pressure to half volume and diluted with 500 mL MTBE. The organic solution is washed with 500 mL water, dried over $Na_2SO_4$, filtered, and concentrated to dryness under reduced pressure. The crude product is purified by flash chromatography on silica, eluting with hexanes/EtOAc (gradient from 1:0 to 9:1). The pure chromatography fractions are combined and concentrated under reduced pressure to give the title compound (144 g, 94.6%, 94.5% ee). Major enantiomer t$_R$=2.20 min; minor enantiomer t$_R$=2.69 min (Chiral SFC Lux Amylose-2, 5% MeOH/CO$_2$, 5 mL/min, 225 nm). $^1$H NMR (DMSO-d$_6$) δ 1.05 (d, J=6.2 Hz, 3H), 1.10 (d, J=6.2 Hz, 3H), 1.19 (d, J=7.0 Hz, 3H), 2.48-2.59 (m, 2H), 3.08-3.19 (m, 1H), 4.74-4.84 (m, 1H), 7.20-7.24 (m, 2H), 7.44-7.48 (m, 2H).

Preparation 7

(3S)-3-(4-bromophenyl)butanoic Acid

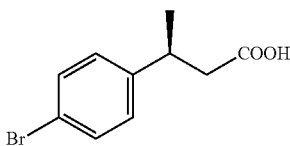

Scheme 2, step B: To a solution of isopropyl (3S)-3-(4-bromophenyl)butanoate (1042 g, 3471.0 mmol) in MeOH (8 L) is added 5 M aqueous NaOH (2 L) while stirring at RT. The reaction is heated to 50° C. under $N_2$ atmosphere for 40 min. After cooling down to 30° C., the reaction mixture is concentrated under reduced pressure and the residue is diluted with 2 L water. The resulting aqueous mixture is extracted once with DCM (~2 L). The aqueous layer is treated with ~1 kg of ice and acidified to pH~4 with conc. HCl (1 L) by slow addition over the course of 20 min. The cloudy aqueous layer is then extracted with DCM (~4 L). The organic layer is dried over Na$_2$SO$_4$, filtered, and concentrated under reduced pressure to a clear tan oil which solidified to an off-white solid. Heptane (~4 L) is added to the solid and the resulting mixture is heated to 45° C. for 2 hr upon which a solid precipitates. The solids are collected by filtration and washed with heptane (200-250 mL). The filtrate is then concentrated to dryness under reduced pressure to give the title compound as an off-white solid (771 g, 91.4%, 99% ee). LC-ES/MS (m/z): 241.0 (M−H). Major enantiomer $t_R$=2.35 min; minor enantiomer $t_R$=2.82 min (Chiral SFC Lux Amylose-2, 5% MeOH/CO$_2$, 5 mL/min, 225 nm). $^1$H NMR (DMSO-d6) δ 1.19 (d, J=7.0 Hz, 3H), 2.48-2.52 (m, 2H), 3.07-3.17 (m, 1H), 7.20-7.25 (m, 2H), 7.44-7.49 (m, 2H), 12.08 (s, 1H). [α]$_D$+25.0° (c=1, MeOH).

Preparation 8

Methyl (3S)-3-(4-bromophenyl)butanoate

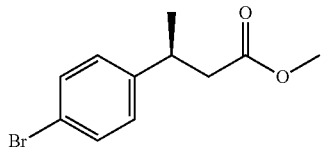

Scheme 2, step C: Concentrated H$_2$SO$_4$ (45 mL, 802 mmol) is added to a solution of (3S)-3-(4-bromophenyl)butanoic acid (450 g, 1851.1 mmol) in MeOH (4.5 L). The mixture is heated at 65° C. for 2 h, cooled to RT, and concentrated under reduced pressure to a dry residue. The solid is diluted with MTBE (2.5 L) and H$_2$O (2.5 L) and the resulting mixture is extracted with MTBE (2×2.5 L). The combined extracts are washed with H$_2$O (2.5 L), dried over MgSO4, filtered, and concentrated under reduced pressure to give the title compound as a light yellow oil (469.8 g, quantitative yield) that may be used without further purification. LC-ES/MS (m/z): 274.0 (M+NH$_4$+). $^1$H NMR (CDCl$_3$) δ 1.27 (d, J=7.0 Hz, 3H), 2.50-2.62 (m, 2H), 3.20-3.30 (m, 1H), 3.61 (s, 3H), 7.07-7.12 (m, 2H), 7.39-7.43 (m, 2H).

Preparation 9

(3S,2R)-methyl 3-(4-bromophenyl)-2-methylbutanoate and (3S,2S)-methyl 3-(4-bromophenyl)-2-methylbutanoate

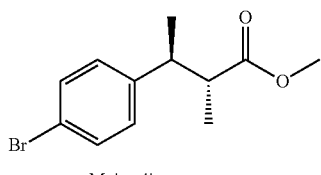

Major diastereomer

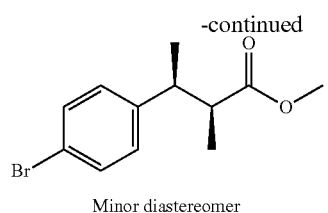

Minor diastereomer

Scheme 2, step D: A 2.5 M solution of n-BuLi in hexanes (1250 mL) is added drop wise to a solution of DIPEA (444 mL, 3150 mmol) in anhydrous THF (2.3 L) at −40° C. over 30 min. After 30 min, a solution of methyl (3S)-3-(4-bromophenyl)butanoate (468.90 g, 1750.7 mmol) in anhydrous THF (3.3 L) is added over 40 min, and the reaction mixture is aged for 40 min at −40° C. CH$_3$I (176 mL, 2798 mmol) is added over 30 min and the mixture is stirred for 15 min at −40° C. The reaction mixture is quenched slowly at −40° C. with MeOH (283 mL) followed by H$_2$O (2.5 L) and the mixture is allowed to warm to RT. The reaction mixture is diluted with H$_2$O (2.5 L) and the resulting layers are separated. The aqueous layer is additionally extracted with MTBE (7.5 L) and the combined organic extracts are washed sequentially with H$_2$O (3 L) and saturated aqueous NaCl (2.5 L). The organic extracts are dried over MgSO$_4$, filtered, and concentrated under reduced pressure to give the title compound as a mixture of diastereomers (7:3) as a light brown oil (489 g, 93%) that may be used without further purification. Major diastereomer $t_R$=1.29 min; minor diastereomer $t_R$=1.32 min (XBRIDGE® C18 column, 3.5 m, 2.1×50 mm, 1.2 mL/min, 50° C., 10-95% 10 mM NH$_4$CO$_3$ (pH 10) in ACN). LC-ES/MS (m/z for $^{79}$Br/$^{81}$Br): 288.0, 290.0 (M+NH$_4$+).

Preparation 10

4-(tert-butyl) 1-methyl (S)-2-((R)-1-(4-bromophenyl)ethyl)-2-methylsuccinate And 4-(tert-butyl) 1-methyl (R)-2-((R)-1-(4-bromophenyl)ethyl)-2-methylsuccinate

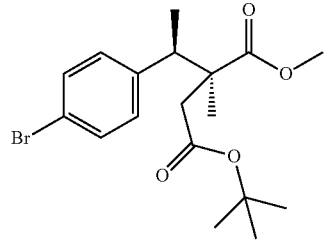

Major diastereomer

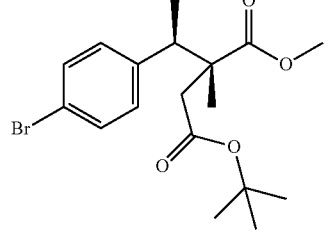

Minor diastereomer

Scheme 2, step E: A 2.5 M solution of n-BuLi in hexanes (1150 mL, 2900 mmol) is added over 20 min to a solution of DIPEA (410 mL, 2910 mmol) in anhydrous THF (3 L) at −40° C. The resulting mixture is stirred at −40° C. for 30 min, and a solution of a mixture of diastereomers methyl (2R/S,3S)-3-(4-bromophenyl)-2-methyl-butanoate (488.00 g, 1619.8 mmol) in anhydrous THF (3 L) is added over a period of 1 hr. The reaction mixture is aged for 45 min at −40° C., and a solution of tert-butyl 2-bromoacetate (391 mL, 2596 mmol) in anhydrous THF (250 mL) is added over 30 min. The resulting mixture is stirred for an additional 30 min at −40° C. MeOH (250 mL) is added followed by H$_2$O (2.5 L), and the resulting mixture is allowed to warm to RT. The mixture is diluted with H$_2$O (2.5 L) and the resulting layers are separated. The aqueous layer is extracted with MTBE (5 L), and the organic extract is washed sequentially with H$_2$O (5 L) followed by saturated aqueous NaCl (2.5 L), dried over MgSO$_4$, filtered, and concentrated under reduced pressure to give the title compound as a mixture of diastereomers as a thick brown oil (786 g, 87%) that may be used without further purification. Major diastereomer t$_R$=1.51 min; minor diastereomer t$_R$=1.53 min (XBRIDGE® C18 column, 3.5 m, 2.1×50 mm, 1.2 mL/min, 50° C., 10-95% 10 mM NH$_4$CO$_3$ (pH 10) in ACN). LC-ES/MS (m/z for $^{79}$Br/$^{81}$Br): 328.8, 330.8 (M-tBu+H).

Preparation 11

(3S,4R)-4-(4-bromophenyl)-3-(methoxycarbonyl)-3-methylpentanoic acid And (3R,4R)-4-(4-bromophenyl)-3-(methoxycarbonyl)-3-methylpentanoic acid

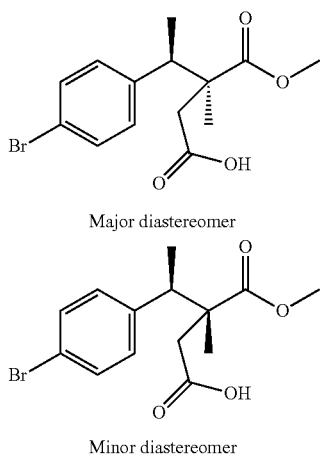

Major diastereomer

Minor diastereomer

Scheme 2: step F: A solution of a mixture of diastereomers 4-(tert-butyl) 1-methyl (R/S)-2-((R)-1-(4-bromophenyl)ethyl)-2-methylsuccinate (785 g, 1406 mmol) in DCM (6 L) is treated with TFA (1.06 L) and stirred at RT for 18 hr. The reaction mixture is washed sequentially with H$_2$O (2×5 L) and saturated aqueous NaCl (5 L). The organic extracts are dried over MgSO$_4$, filtered, and concentrated under reduced pressure to give the title compound as a mixture of diastereomers (8:2) as a dark brown gum (604 g, 91%) that may be used without further purification. LC-ES/MS (m/z for $^{79}$Br/$^{81}$Br): 329.0, 331.0 (M+H).

Preparation 12

Methyl (2S)-4-amino-2-[(1R)-1-(4-bromophenyl)ethyl]-2-methyl-4-oxo-butanoate And Methyl (2R)-4-amino-2-[(1R)-1-(4-bromophenyl)ethyl]-2-methyl-4-oxo-butanoate

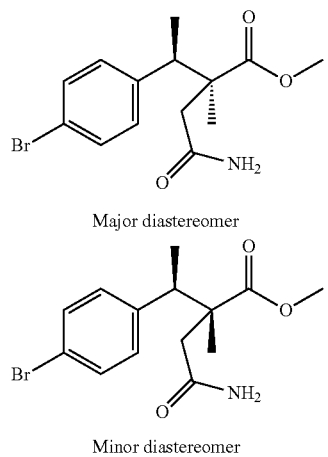

Major diastereomer

Minor diastereomer

Scheme 2, step G: To a mixture of diastereomers (3R/S, 4R)-4-(4-bromophenyl)-3-methoxycarbonyl-3-methylpentanoic acid (603 g, 1282 mmol) and TEA (550 mL, 3870 mmol) in anhydrous DMF (4 L) at 0° C. is added HATU (597 g, 1538.69 mmol) over 15 min. The reaction mixture is aged at room temperature for 2 hr. A solution of 7 M NH$_3$/MeOH (1.83 L) is added over 30 min at 10° C., and the resulting mixture is warmed to RT and stirred for 1 h. The reaction mixture is cooled to 10° C. and then diluted slowly with DCM (5 L) followed by H$_2$O (5 L). The resulting layers are separated, and the aqueous layer is additionally extracted with DCM (2.5 L). The combined extracts are washed sequentially with H$_2$O (5 L) and saturated aqueous NaCl (5 L), dried over MgSO$_4$, filtered, and concentrated under reduced pressure to give the title compound as a mixture of diastereomers (8:2) as a dark gum (520 g, 87%) that may be used without further purification. Major diastereomer t$_R$=0.97 min; minor diastereomer t$_R$=0.99 min (XBRIDGE® C18 column, 3.5 m, 2.1×50 mm, 1.2 mL/min, 50° C., 10-95% 10 mM NH$_4$CO$_3$ (pH 10) in ACN). LC-ES/MS (m/z for $^{71}$Br/$^{81}$Br) 328.0/330.0 (M+H/M+H+2).

Preparation 13

(3S)-3-[(R)-1-(4-bromophenyl)ethyl]-3-methyl-pyrrolidine-2,5-dione and (3R)-3-[(1R)-1-(4-bromophenyl)ethyl]-3-methyl-pyrrolidine-2,5-dione

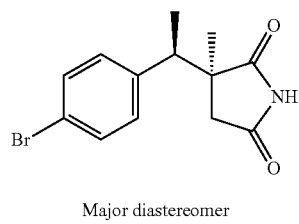

Major diastereomer

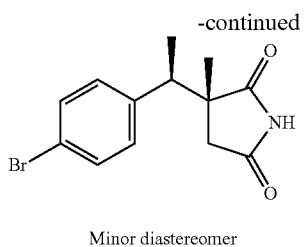

Minor diastereomer

Scheme 2, step H: To a mixture of diastereomers methyl (2R/S)-4-amino-2-[(R)-1-(4-bromophenyl)ethyl]-2-methyl-4-oxo-butanoate (519 g, 1107 mmol) dissolved in THF (4.2 L) and H$_2$O (4.2 L) is added Na$_2$CO$_3$ (293 g, 2764.46 mmol) and the mixture is heated at 60° C. for 2 hr. The reaction is cooled to RT and extracted with EtOAc (2.5 L). The organic layer is washed with H$_2$O (3 L). The resulting aqueous extract is extracted with EtOAc (5 L) and the combined organic extracts are dried over MgSO$_4$, filtered, and concentrated under reduced pressure to give a crude mixture of the two diastereomers that are separated by SFC [Column: AS-H, 150×50 mm; 10% EtOH (0.2% DEMA), 340 g/min; BPR 150 bar, Inj vol: 4 ml; 220 nm]. (3R)-3-[(1R)-1-(4-bromophenyl)ethyl]-3-methyl-pyrrolidine-2,5-dione: first eluting compound (43.8 g, 11%). LC-ES/MS (m/z for $^{79}$Br/$^{81}$Br): 313.0, 315.0 (M+H). $^1$H NMR (CDCl$_3$) δ 1.33 (d, J=7.2 Hz, 3H), 1.40 (s, 3H), 2.34 (d, J=18.4 Hz, 1H), 2.80 (J=18.4 Hz, 1H), 3.23 (q, J=7.2 Hz, 1H), 7.07 (d, 2H), 7.40 (d, 2H), 7.54 (br-s, 1H). (3S)-3-[(1R)-1-(4-bromophenyl)ethyl]-3-methyl-pyrrolidine-2,5-dione: second eluting compound (241.8 g, 55%). LC-ES/MS (m/z for $^{79}$Br/$^{81}$Br): 313.0, 315.0 (M+H). $^1$H NMR (CDCl$_3$): 1.23 (s, 3H), 1.30 (d, J=7.1 Hz, 3H), 2.21 (d, J=18.4 Hz, 1H), 2.96 (d, J=18.4 Hz, 1H), 3.14 (q, J=7.1 Hz, 1H), 7.04-7.09 (m, 2H), 7.42-7.48 (m, 2H), 8.09 (br-s, 1H).

Preparation 14

2,6-Dimethylpyridine-4-carbonitrile

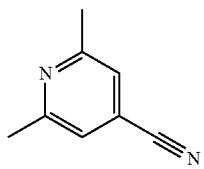

Scheme 3, step A: Zinc cyanide (3.82 g, 31.9 mmol) is added to a mixture of 4-bromo-2,6-dimethylpyridine (5.09 g, 26.5 mmol) and DMF (40 mL) stirring under nitrogen at RT. Nitrogen is bubbled through the stirred suspension for 15 min, and tetrakis(triphenylphosphine) palladium(0) (1.54 g, 1.33 mmol) is added. After heating the reaction mixture at 120° C. for 5.5 hr, the mixture is cooled to RT and diluted with EtOAc (150 mL). The solids are removed via paper filtration and the filter cake is washed with EtOAc (50 mL). The combined organic filtrate and wash is washed sequentially with 15% aqueous NH$_3$ (2×50 mL), water (50 mL) and saturated aqueous NaCl, dried over Na$_2$SO$_4$, filtered, and concentrated under reduced pressure to give a yellow solid. The crude product is purified flash chromatography on silica, eluting with hexanes/ethyl acetate (gradient from 9:1 to 1:1). The pure chromatography fractions are combined and concentrated under reduced pressure to give the title compound (2.79 g, 77%). $^1$H NMR (CDCl$_3$): δ 2.61 (s, 6H), 7.21 (s, 2H).

Alternative Procedure for Preparation 14

Scheme 3, step A: 4-Bromo-2,6-dimethylpyridine (235.0 g, 1263.1 mmol) is dissolved in anhydrous DMF (250 mL) in a three-necked round bottom flask equipped with a mechanical stirrer, reflux condenser, and N$_2$ inlet and N$_2$ is bubbled through the solution for 20 min. A portion of the solution (~150 mL) is transferred to an addition funnel via a cannula under N$_2$. Zinc cyanide (150.0 g, 1277.4 mmol) and tetrakis(triphenylphosphine)palladium (0) (15.0 g, 13.0 mmol) is added to the reaction mixture and sparged by bubbling N2 into the mixture for 15 min. The reaction mixture is heated to 90° C. The DMF solution of 4-bromo-2,6-dimethylpyridine is added drop wise over 30 min and heating is continued overnight. The mixture is cooled to RT, MTBE (~2 L) is added, followed by water (1.5 L) and 30% aqueous NH$_4$OH (800 mL); the resulting mixture is stirred at RT for 30 min. The layers are separated, the aqueous layer is extracted once with MTBE (~2 L); the organic phases are combined, washed once with 10% aqueous NH$_4$OH (2 L), dried over Na$_2$SO$_4$, filtered, and the filtrate is evaporated under reduced pressure to obtain the crude title compound (153 g, 91.7% yield) as a pale yellow solid, contaminated with ~10% triphenylphosphine byproduct, which is suitable for use without additional purification. $^1$H NMR (CDCl$_3$): δ 2.61 (s, 6H), 7.21 (s, 2H).

Preparation 15

1-(2,6-Dimethylpyridin-4-yl)methamine Dihydrochloride

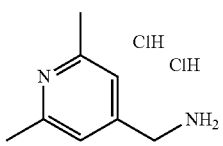

Scheme 3, step B: A solution of 2,6-dimethylpyridine-4-carbonitrile (2.26 g, 16.7 mmol) in EtOH (40 mL) is added to a suspension of 10% Pd on carbon (405 mg), EtOH (10 mL), and concentrated aqueous HCl (6.9 mL). The reaction vessel is evacuated, filled with nitrogen, and H$_2$ (55 psi) is introduced, with stirring of the subsequent reaction mixture at RT for 16 hr. The reaction mixture is filtered through diatomaceous earth. The filter cake is washed with MeOH and the combined filtrate is concentrated to give a yellow solid. The crude material is triturated with boiling 30% EtOH/EtOAc, cooled to RT, and collected via filtration to give the title compound (2.64 g, 75%). LC-ES/MS (m/z): 137.0 (M+H).

Alternative Procedure for Preparation 15

Scheme 3, step B: The following may be run in two batches and the two batches combined after the complete hydrogenation reaction: 2,6-Dimethylpyridine-4-carbonitrile (77.39 g, 527.0 mmol) is added to a 2 L Parr autoclave, equipped with a mechanical stirrer, containing a mixture of 10% Pd/C (45.8 g) in MeOH (800 mL) and a 4M solution of HCl in dioxane (500 mL). The autoclave is sealed, the resulting mixture is purged thoroughly with N₂ followed by H₂, and pressurized with H₂ to 60 psi with stirring at RT overnight. The reaction mixture is filtered and the filtrate is evaporated under reduced pressure. MeOH (~250 mL) is added to the resulting residue and stirred for 15 hr, and MTBE (2.5 L) is added slowly. The mixture is stirred at RT for 1hr, filtered, and the solids are washed with MTBE (1 L). The solids are dried in vacuo at RT overnight to obtain the title compound as a pale yellow solid (217.0 g, 91.6% yield, combination of two runs), suitable for use without additional purification. LC-ES/MS (m/z): 137.2 (M+H), 92.5% purity, with 7.5% triphenylphosphine impurity present (1.57 min, m/z: 263.0).

Preparation 16

6-cyclopropyl-4-methyl-pyridine-2-carbonitrile

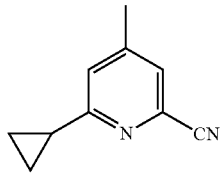

Scheme 4, step A: Cyclopropylboronic acid (1.98 g, 21.9 mmol) is added to a mixture of 6-chloro-4-methyl-pyridine-2-carbonitrile (US 20140256734 A1, 2.15 g, 13.7 mmol), K₃PO₄ (5.98 g, 27.3 mmol), toluene (40 mL) and water (2 mL) stirring under nitrogen at RT. Nitrogen is bubbled through the stirred suspension for 10 min, and palladium(II) acetate (0.313 g, 1.37 mmol) and tricyclohexylphosphonium tetrafluoroborate (1.02 g, 2.73 mmol) are added. After heating the reaction mixture under nitrogen at 110° C. for 15.5 hr, the mixture is cooled to RT and diluted with EtOAc (50 mL). The solids are removed via diatomaceous earth filtration and the filter cake is washed with EtOAc (20 mL). The combined organic filtrate and wash is washed with saturated aqueous NaCl, dried over Na₂SO₄, filtered, and concentrated under reduced pressure to give an amber oil. The crude product is purified by flash chromatography on silica, eluting with hexanes/ethyl acetate (gradient from 50:1 to 2:1). The pure chromatography fractions are combined and concentrated under reduced pressure to give the title compound (1.52 g, 70% yield). LC-ES/MS (m/z): 159.0 (M+H).

Preparation 17

(6-cyclopropyl-4-methyl-2-pyridyl)methanamine Dihydrochloride

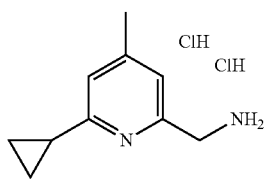

Scheme 4, step B: Prepare from 6-cyclopropyl-4-methyl-pyridine-2-carbonitrile (1.52 g, 9.63 mmol) essentially by the method described in Preparation 15 to obtain the title compound (1.86 g, 82% yield). LC-ES/MS (m/z): 163.0 (M+H).

Preparation 18

2-cyclopropyl-6-methyl-pyridine-4-carbonitrile
AG2-E14219-088

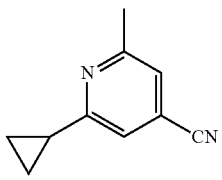

Scheme 4, step A: Prepare from 2-chloro-6-methyl-pyridine-4-carbonitrile (J. Med. Chem., 59(1), 313-327, 2016, 2.0 g, 12.7 mmol) essentially by the method described in Preparation 16 to give the title compound (1.66 g, 82% yield). ¹H NMR (CDCl₃): δ 1.05-1.06 (m, 4H) 2.03-2.09 (m, 1H), 2.54 (s, 3H), 7.11 (s, 1H), 7.14 (s, 1H).

Preparation 19

(2-cyclopropyl-6-methyl-4-pyridyl)methanamine Dihydrochloride 3344731, AG2-E14219-090

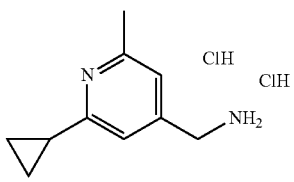

Scheme 4, step B: Prepare from 2-cyclopropyl-6-methyl-pyridine-4-carbonitrile (2.52 g, 15.9 mmol) essentially by the method described in Preparation 15 to obtain the title compound (3.57 g, 95% yield). LC-ES/MS (m/z): 163.0 (M+H).

Preparation 20

Methyl 2-isopropyl-6-methyl-pyridine-4-carboxylate

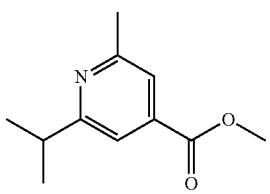

A 2M solution of isopropyl magnesium chloride in THF (7.53 mL, 15.1 mmol) is added drop wise, over 8 minutes, to a mixture of methyl 2-chloro-6-methyl-pyridine-4-carboxylate (1.92 g, 10.0 mmol), MnCl₂ (0.065 g, 0.502 mmol) and THF (25 mL) stirring under nitrogen in an ice/water bath. After stirring in the cold bath for 4 hours, the reaction is quenched with saturated aqueous NH₄Cl and extracted with EtOAc (2×50 mL). The combined extract is washed with saturated aqueous NaCl, dried over Na₂SO₄, filtered, and concentrated under reduced pressure to give an amber oil. The crude product is purified by flash chromatography on silica, eluting with hexanes/ethyl acetate (gradient from 50:1 to 2:1). The pure chromatography fractions are combined and concentrated under reduced pressure to give the title compound (0.683 g, 35% yield). ¹H NMR (CDCl₃): δ 1.34 (d, J=6.9 Hz, 6H) 2.63 (s, 3H), 3.12-3.19 (m, 1H), 3.96 (s, 3H), 7.54 (s, 1H), 7.56 (s, 1H).

Preparation 21

2-[(2-isopropyl-6-methyl-4-pyridyl)methyl]isoindoline-1,3-dione

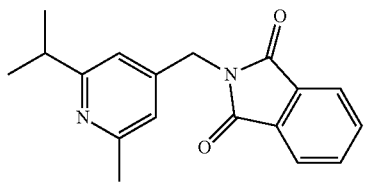 [SMILES: Cc1cc(CN2C(=O)c3ccccc3C2=O)cc(C(C)C)n1]

Sodium borohydride (0.231 g, 6.01 mmol) is added to a solution of methyl 2-isopropyl-6-methyl-pyridine-4-carboxylate (0.683 g, 3.53 mmol) in EtOH (15 mL) at RT. After stirring overnight, the solvent is removed under reduced pressure, the remaining oil diluted with saturated aqueous NaCl and extracted with EtOAc (2×50 mL). The combined extract is dried over Na₂SO₄, filtered, and concentrated under reduced pressure to give 652 mg of crude (2-isopropyl-6-methyl-4-pyridyl)methanol as an amber solid. The crude alcohol is dissolved in DCM (20 mL) and treated with thionyl chloride (0.514 mL, 7.02 mmol). After stirring at RT for 4 hours, the reaction mixture was concentrated under reduced pressure; dissolved in toluene and reconcentrated (2×). The crude alkyl chloride is dissolved in DMF (10 mL) and potassium phthalimide (1.32 g, 7.02 mmol) is added. The suspension is stirred at RT for 3.5 hours and diluted with water (100 mL). The resulting suspension is stirred at RT for one hour and the solid collected via filtration. The crude product is purified by flash chromatography on silica, eluting with DCM/ethyl acetate (gradient from 50:1 to 4:1). The pure chromatography fractions are combined and concentrated under reduced pressure to give the title compound (0.332 g, 32% yield). ¹H NMR (CDCl₃): δ 1.29 (d, J=6.9 Hz, 6H), 2.51 (s, 3H), 3.06-3.08 (m, 1H), 4.80 (s, 2H), 6.96 (s, 1H), 7.00 (s, 1H), 7.76-7.79 (m, 2H), 7.89-7.92 (m, 2H).

Preparation 22

(2-isopropyl-6-methyl-4-pyridyl)methanamine AG2-E14044-027

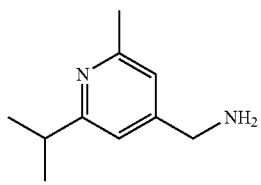

Hydrazine monohydrate (0.70 mL, 1.41 mmol) is added to a suspension of 2-[(2-isopropyl-6-methyl-4-pyridyl)methyl]isoindoline-1,3-dione (0.332 g, 1.13 mmol) and EtOH (10 mL) at RT. After refluxing for 1.5 hours, the reaction mixture is cooled to RT and the solids are removed by paper filtration. The filter cake is washed with EtOH (10 mL) and the combined filtrate/wash is concentrated under reduced pressure to give the title compound (0.179 g, 96% yield). ¹H NMR (CDCl₃): δ 1.31 (d, J=6.8 Hz, 6H), 1.56-1.63 (br-s, 2H), 2.54 (s, 3H), 3.02-3.09 (m, 1H), 3.86 (s, 2H), 6.95 (s, 2H).

Preparation 23

(1 S)-1-(6-bromopyridin-3-yl)ethanol

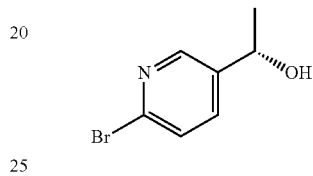

Scheme 6, step A: A solution of chloro{(R)-(+)-2,2'-bis[di(3,5-xylyl)phosphino]-1,1'-binaphthyl}[(2R)-(−)-1-(4-methoxyphenyl)-1-(4-methoxyphenyl-kC)-3-methyl-1,2-butanediamine]ruthenium(II) (103 mg, 0.087 mmol) and KOᵗBu (1.0 M in t-BuOH, 0.88 mL, 0.88 mmol) in anhydrous 2-propanol (15 mL) under nitrogen is added to a solution of 1-(6-bromopyridin-3-yl)ethanone (23.5 g, 117.0 mmol) in anhydrous EtOH (100 mL)/anhydrous 2-propanol (85 mL) in a 600 mL Parr autoclave under nitrogen. The autoclave is sealed, evacuated, pressurized to 207 kPa with hydrogen, and stirred at RT for about 6 hr. The reaction mixture is concentrated under reduced pressure to give a solid residue and dried under vacuum overnight. The residue is purified by flash chromatography over silica, eluting with DCM/MTBE (gradient from 9:1 to 3:1) to give the title compound (23.7 g, 94% yield). LC-ES/MS (m/z for ⁷⁹Br/⁸¹Br): 202.0/204.0 (M+H). Chiral HPLC indicates 99.3% ee; t_R=6.32 min [254 nm; LC Column: CHIRALCEL® OD-H 4.6×150 mm; 5.0 µL injection; 10% 2-propanol in heptane (containing 0.2% DMEA); Column Temp: 25° C.; Flow Rate: 1.0 mL/min].

Preparation 24

(1S)-1-(6-bromopyridin-3-yl)ethyl Methanesulfonate

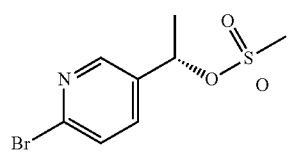

Scheme 6, step B: To a stirred solution of (1S)-1-(6-bromopyridin-3-yl)ethanol (3.00 g, 14.8 mmol) and TEA (2.69 mL, 19.3 mmol) in DCM (30 mL) at 0° C. is added methanesulfonyl chloride (1.38 mL, 17.8 mmol). After 2 hr at 0° C., water and DCM are added and the layers are separated. The aqueous layer is extracted with DCM. The organic layers are combined and washed sequentially with saturated aqueous NaHCO₃ and saturated NaCl, dried over Na₂SO₄; filtered, and concentrated under reduced pressure to give the title compound (4.13 g, 99% yield). LC-ES/MS (m/z for ⁷⁹Br/⁸¹Br): 280.0/282.0 (M+H). ¹H NMR (CDCl₃) δ 1.74 (d, J=6.6 Hz, 3H), 2.93 (s, 3H), 5.76 (q, J=6.6 Hz, 1H), 7.54 (d, J=8.3 Hz, 1H), 7.62 (dd, J=2.5, 8.3 Hz, 1H), 8.41 (d, J=2.5 Hz, 1H).

Preparation 25

Dimethyl 2-[(1R)-1-(6-bromo-3-pyridyl)ethyl]-2-methyl-propanedioate

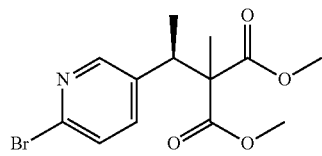 [SMILES: COC(=O)C(C)(C(=O)OC)[C@H](C)c1ccc(Br)nc1]

Scheme 6, step C: Prepare from (1S)-1-(6-bromopyridin-3-yl)ethyl methanesulfonate (17.9 g, 63.9 mmol) essentially by the method described in Preparation 1 to obtain the title compound (18.9 g, 89% yield). %). ¹H NMR (CDCl₃): δ 1.39 (d, J=7.2 Hz, 3H), 1.40 (s, 3H), 3.66 (s, 3H), 3.68-3.71 (m, 1H), 3.76 (s, 3H), 7.42 (d, J=8.3 Hz, 1H), 7.48 (dd, J=2.5, 8.3 Hz, 1H), 8.25 (d, J=2.4 Hz, 1H).

Preparation 26

Methyl (3S)-3-(6-bromo-3-pyridyl)-2-methyl-butanoate

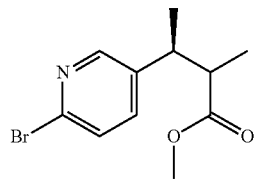

Scheme 6, step D: Prepare from dimethyl 2-[(1R)-1-(6-bromo-3-pyridyl)ethyl]-2-methyl-propanedioate (18.9 g, 57.2 mmol) essentially by the method described in Preparation 2 to obtain the title compound (12.5 g, 80% yield) as a mixture of diastereomers. LC-ES/MS (m/z): 271.9 (M+H).

Preparation 27

Methyl (3R)-3-(6-bromo-3-pyridyl)-2-(cyanomethyl)-2-methyl-butanoate

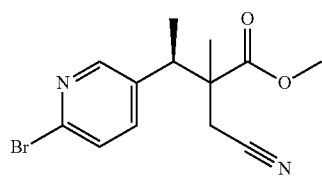 [SMILES: COC(=O)C(C)(CC#N)[C@H](C)c1ccc(Br)nc1]

Scheme 6, step E: Prepare from methyl (3S)-3-(6-bromo-3-pyridyl)-2-methyl-butanoate (12.5 g, 46.1 mmol) essentially by the method described in Preparation 3 to obtain the title compound (7.66 g, 53% yield) as a mixture of diastereomers. ¹H NMR (CDCl₃): δ 1.36-1.41 (m, 6H) 2.36-2.45 (m, 1H), 2.65-2.73 (m, 1H), 3.17-3.24 (m, 1H), 3.74-3.76 (s, 3H), 7.35-7.39 (m, 1H), 7.47 (d, J=8.2 Hz, 1H), 8.20 (d, J=2.2 Hz, 1H).

Preparation 28

(3S)-3-[(1R)-1-(6-bromo-3-pyridyl)ethyl]-3-methyl-pyrrolidine-2,5-dione (Major Diastereomer) and (3R)-3-[(1R)-1-(6-bromo-3-pyridyl)ethyl]-3-methyl-pyrrolidine-2,5-dione (Minor Diastereomer)

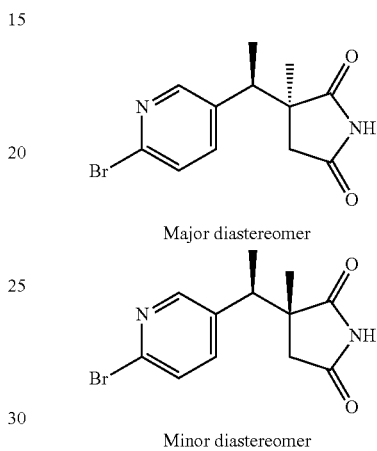

Major diastereomer

Minor diastereomer

Scheme 6, step F: Prepare from methyl (3R)-3-(6-bromo-3-pyridyl)-2-(cyanomethyl)-2-methyl-butanoate (7.66 g, 24.6 mmol) essentially by the method described in Preparation 4 to give 6.57 g of a diastereomeric mixture. Diastereomers are separated on a Chiralpak AD column (8×35 cm, 100% EtOH) to give the minor diastereomer as the first eluting material, (3R)-3-[(1R)-1-(6-bromo-3-pyridyl)ethyl]-3-methyl-pyrrolidine-2,5-dione, (0.74 g, 10%) and the major diastereomer as the second eluting material, (3S)-3-[(1R)-1-(6-bromo-3-pyridyl)ethyl]-3-methyl-pyrrolidine-2,5-dione, (5.21 g, 71%).

Major isomer: ¹H NMR (CDCl₃): δ 1.27 (s, 3H), 1.36 (d, J=7.1 Hz, 3H), 2.28 (d, J=18.2 Hz, 1H), 2.93 (d, J=18.3 Hz, 1H), 3.22 (q, J=7.2 Hz, 1H), 7.41 (dd, J=2.6, 8.2 Hz, 1H), 7.49 (d, J=8.3 Hz, 1H), 7.87-7.89 (br-s, 1H), 8.26 (d, J=2.4 Hz, 1H).

Minor isomer: ¹H NMR (CDCl₃): δ 1.39 (d, J=7.3 Hz, 3H), 1.44 (s, 3H), 2.46 (d, J=18.4 Hz, 1H), 2.76 (d, J=18.5 Hz, 1H), 3.25 (q, J=7.3 Hz, 1H), 7.43-7.50 (m, 2H), 7.98-8.00 (br-s, 1H), 8.25 (d, J=2.4 Hz, 1H).

Preparation 29

Methyl 5-[(1R)-1-[(3S)-3-methyl-2,5-dioxo-pyrrolidin-3-yl]ethyl]pyridine-2-carboxylate

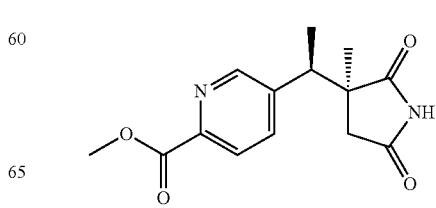

Scheme 6, step G: Scheme 3, step B: Palladium(II) acetate (115 mg, 0.49 mmol), 1,1'-bis(diphenylphosphino)ferrocene (340 mg, 0.6 mmol), (3R)-3-[(1R)-1-(6-bromopyridin-3-yl)ethyl]-3-methyl-1-{[2-(trimethylsilyl)ethoxy]methyl}-1,3-dihydro-2H-pyrrolo[2,3-b]pyridin-2-one (1.5 g, 5.07 mmol), anhydrous MeOH (25 mL), anhydrous ACN (40 mL), and TEA (1.8 mL, 13 mmol) are combined in a 300 mL Parr autoclave with a mechanical stirrer. The autoclave is sealed, purged with CO, pressurized to 100 psi with CO, and heated to 85° C. with stirring. After 1 hr, the reaction mixture is cooled to room temperature overnight and filtered. The filtrate is concentrated under reduced pressure to give a solid residue. The residue is suspended in EtOAc (200 mL) and filtered again. The filtrate is concentrated under reduced pressure to give an orange residue. The orange residue is purified by flash chromatography over silica, eluting with a gradient of 5-60% EtOAc in DCM over 35 min, to give the title compound (1.34 g, 95% yield), after solvent evaporation of the desired fractions. $^1$H NMR (CDCl$_3$): δ 1.27 (s, 3H) 1.41 (d, J=7.1 Hz, 3H), 2.29 (d, J=18.3 Hz, 1H), 2.98 (d, J=18.3 Hz, 1H), 3.34 (q, J=7.1 Hz, 1H), 4.04 (s, 3H), 7.71 (dd, J=2.2, 8.1 Hz, 1H), 8.14 (d, J=8.1 Hz, 1H), 8.18-8.29 (br-s, 1H), 8.64 (d, J=1.9 Hz, 1H).

Preparation 30

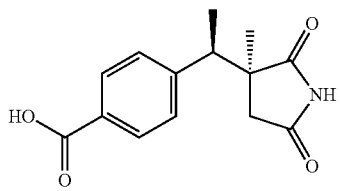 [SMILES: C[C@H](c1ccc(C(=O)O)cc1)[C@]1(C)CC(=O)NC1=O]

Scheme 6, step H: Solid LiOH hydrate (3.16 g, 75.3 mmol) is added to a solution of methyl 4-[(1R)-1-[(3S)-3-methyl-2,5-dioxo-pyrrolidin-3-yl]ethyl]benzoate (6.9 g, 25.1 mmol) dissolved in a mixture of THF (28 mL) and water (12 mL). The resulting mixture is stirred at RT overnight, the pH is adjusted to ~3 with 1N aqueous HCl, and the solvents are removed under reduced pressure. The resulting residue is dried in a vacuum oven at 45° C. overnight to obtain the title compound (5.96 g, 91% yield) suitable for further use without additional purification. LC-ES/MS (m/z): 260.0 (M–H).

Preparation 31

(6-chloro-4-methyl-2-pyridyl)methanol

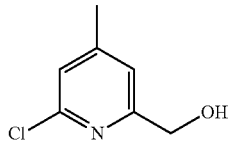

Scheme 5, step A (Y=CH, Z=N): Sodium borohydride (905 mg, 23.4 mmol) is added in one portion to a solution of ethyl 6-chloro-4-methylpyridine-2-carboxylate (2.81 g, 13.8 mmol) dissolved in EtOH (25 m L). the reaction mixture is stirred for 18 hr at RT and concentrated under reduced pressure. The resulting residue is diluted with saturated aqueous NaCl and extracted twice with EtOAc, the organic extracts are dried over Na$_2$SO$_4$, filtered, and concentrated under reduced pressure to obtain the title compound suitable for use without additional purification. LC-ES/MS (m/z $^{35}$Cl/$^{37}$Cl): 158.0/160.0 (M+H).

Preparation 32

2-chloro-6-(chloromethyl)-4-methyl-pyridine

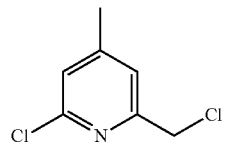

Scheme 5, step B (Y=CH, Z=N): To a solution of (6-chloro-4-methyl-2-pyridyl)methanol (2.3 g, 13.8 mmol) in DCM (25 mL) under an atmosphere of nitrogen is added thionyl chloride (2 mL, 27.5 mmol). The reaction mixture is stirred at RT for 4.5 hr, concentrated under reduced pressure, and the residue reconstituted in toluene and reconcentrated twice more under reduced pressure, then dried in a vacuum oven at 45° C. overnight, to obtain the title compound (2.36 g, 97% yield) as a light amber oil. $^1$H NMR (CDCl$_3$): δ 2.37 (s, 3H), 4.59 (s, 2H), 7.11 (s, 1H), 7.24 (s, 1H).

Preparation 33

2-[(6-chloro-4-methyl-2-pyridyl)methyl]isoindoline-1,3-dione

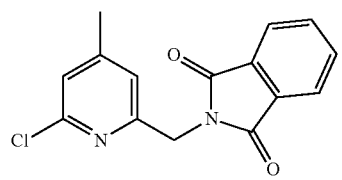 [SMILES: Cc1cc(Cl)nc(CN2C(=O)c3ccccc3C2=O)c1]

Scheme 5, step C (Y=CH, Z=N): Potassium phthalimide (2.98 g, 15.8 mmol) is added to a solution of 2-chloro-6-(chloromethyl)-4-methyl-pyridine (2.36 g, 13.1 mmol) in DMF (25 mL) under a stream of nitrogen at RT. Stirring is continued for 3.5 hr, and additional potassium phthalimide (523 mg, 2.8 mmol) is added as stirring at RT is continued over 72 hr. The reaction mixture is diluted with water (150 mL) and the mixture is stirred for 30 min. The resulting white precipitate is collected by vacuum filtration, and the solids are dried in a vacuum oven at 35° C. overnight to obtain the title compound as a white solid (3.6 g, 96% yield). $^1$H NMR (CDCl$_3$): δ 2.29 (s, 3H), 4.94 (s, 2H), 6.92 (s, 1H), 7.04 (s, 1H), 7.73-7.79 (m, 2H), 7.88-7.93 (m, 2H).

Preparation 34

6-[(1,3-dioxoisoindolin-2-yl)methyl]-4-methyl-pyridine-2-carbonitrile

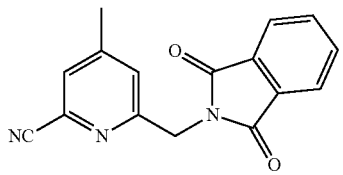 [SMILES: Cc1cc(C#N)nc(CN2C(=O)c3ccccc3C2=O)c1]

Scheme 5, step D (Y=CH, Z=N): Nitrogen is bubbled through a suspension of 2-[(6-chloro-4-methyl-2-pyridyl)methyl]isoindoline-1,3-dione (1.3 g, 4.6 mmol), zinc cyanide (0.23 mL, 3.5 mmol), [1,1'-bis(diphenylphosphino)ferrocene]palladium(II) dichloride (174 mg, 0.23 mmol) and elemental zinc (76 mg, 1.2 mmol) in DMF for 10 min. The reaction mixture is heated in an oil bath at 120° C. for 5.5 hr. The mixture is cooled to RT, diluted with EtOAc (100 mL), and filtered through paper to remove any insolubles. The filtrate is washed sequentially with 15% aqueous $NH_4OH$, water, and saturated aqueous NaCl; the organic layer is dried over $Na_2SO_4$, filtered, and concentrated under reduced pressure. The resulting residue is purified by flash chromatography on silica gel, eluting with 10-60% EtOAc in hexanes over 35 min to obtain the title compound (1.04 g, 80.5% yield) as a light yellow solid after solvent evaporation. $^1H$ NMR ($CDCl_3$): δ 2.39 (s, 3H), 5.00 (s, 2H), 7.28 (s, 1H), 7.40 (s, 1H), 7.74-7.80 (m, 2H), 7.88-7.94 (m, 2H).

Preparation 35

6-(aminomethyl)-4-methyl-pyridine-2-carbonitrile Dihrochloride

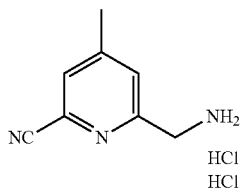

Scheme 5, step E (Y=CH, Z=N): Hydrazine hydrate (371 μL, 7.5 mmol) is added to a suspension of 6-[(1,3-dioxoisoindolin-2-yl)methyl]-4-methyl-pyridine-2-carbonitrile (1.04 g, 3.7 mmol) in EtOH (20 mL) and the resulting mixture is heated at reflux for 1.5 hr. The reaction mixture is cooled, filtered, and the filtrate is concentrated under reduced pressure. The resulting residue is dissolved in MeOH (~25 mL) and loaded onto an SCX column (10 g), eluting with 1:1 MeOH:DCM (30 mL), MeOH (20 mL), and 2M $NH_3$/MeOH (50 mL). The methanolic ammonia fractions are concentrated under reduced pressure to give a light yellow oil which is dissolved in THF (15 mL) and treated with 4N HCl in 1,4-dioxane (2.5 mL). the mixture is stirred at RT for 15 min, and the resulting solids are collected by vacuum filtration. The crystalline filter cake is dried in a vacuum oven at 45° C. overnight to obtain the title compound (541 mg, 66% yield) as a pale yellow solid. $^1H$ NMR (DMSO-$d_6$): δ 2.41 (s, 3H), 4.22 (q, J=5.6 Hz, 2H), 7.70 (s, 1H), 7.95 (s, 1H), 8.55 (br s, 2H).

Preparation 36

(2-chloro-6-methylpyridin-4-yl)methanol

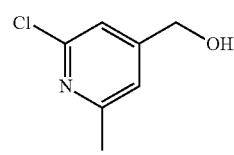

Scheme 5, step A (Y=N, CH): Prepare from methyl 2-chloro-6-methylpyridine-4-carboxylate (2.4 g, 12.5 mmol) essentially by the method described in Preparation 31 to obtain the title compound (2.0 g, 97% yield). $^1H$ NMR ($CDCl_3$): δ 2.54 (s, 3H), 4.71 (s, 2H), 7.07 (s, 1H), 7.16 (s, 1H).

Preparation 37

2-chloro-4-(chloromethyl)-6-methylpyridine

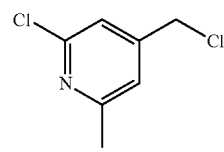

Scheme 5, step B (Y=N, CH): Prepare from (2-chloro-6-methylpyridin-4-yl)methanol (1.97 g, 12.1 mmol) essentially by the method described in Preparation 32 to obtain the title compound (2.28 g, 99.5% yield). $^1H$ NMR (DMSO-$d_6$): δ 2.45 (s, 3H), 4.74 (s, 2H), 7.33 (s, 1H), 7.37 (s, 1H).

Preparation 38

2-[(2-chloro-6-methyl-4-pyridyl)methyl]isoindoline-1,3-dione

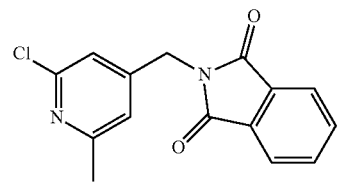 [SMILES: Cc1cc(CN2C(=O)c3ccccc3C2=O)cc(Cl)n1]

Scheme 5, step C (Y=N, CH): Prepare from 2-chloro-4-(chloromethyl)-6-methylpyridine (2.28 g, 12 mmol) essentially by the method described in Preparation 33 to obtain the title compound (3.67 g, 98.7% yield). $^1H$ NMR (DMSO-$d_6$): δ 2.41 (s, 3H), 4.77 (s, 2H), 7.21 (s, 1H), 7.30 (s, 1H), 7.85-7.94 (m, 4H).

Preparation 39

4-[(1,3-dioxoisoindolin-2-yl)methyl]-6-methyl-pyridine-2-carbonitrile

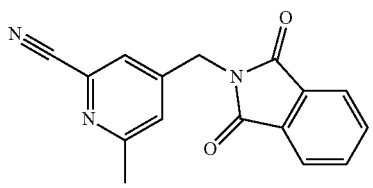 [SMILES: Cc1cc(CN2C(=O)c3ccccc3C2=O)cc(C#N)n1]

Scheme 5, step D (Y=N, CH): Prepare from 2-[(2-chloro-6-methyl-4-pyridyl)methyl]isoindoline-1,3-dione (3.66 g, 11.9 mmol) essentially by the method described in Preparation 34 to obtain the title compound (1.7 g, 51.5% yield). $^1$H NMR (CDCl$_3$): δ 2.58 (s, 3H), 4.84 (s, 2H), 7.36 (s, 1H), 7.51 (s, 1H), 7.75-7.81 (m, 2H), 7.88-7.93 (m, 2H).

Preparation 40

4-(aminomethyl)-6-methylpyridine-2-carbonitrile

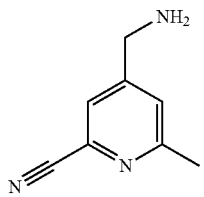

Scheme 5, step E (Y=N, CH): Prepare from 4-[(1,3-dioxoisoindolin-2-yl)methyl]-6-methyl-pyridine-2-carbonitrile (1.69 g, 6.1 mmol) essentially by the method described in Preparation 35 to obtain the title compound (379 mg, 41% yield). $^1$H NMR (CDCl$_3$): δ 1.47 (br-s, 2H), 2.59 (s, 3H), 3.94 (s, 2H), 7.36 (s, 1H), 7.53 (s, 1H).

Preparation 41

2-ethyl-6-methylpyridine-4-carbonitrile

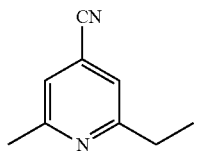

Scheme 4, step A: Ethylmagnesium bromide (18 ml, 17.7 mmol) is added in portions to a mixture of 2-chloro-6-methylisonicotinonitrile (Bioorganic & Medicinal Chemistry Letters, 20(2), 576-580; 2010) (10.0 g, 63.7 mmol), 1-methyl-2-pyrrolidinone (10 ml), THF (10 mL) and Iron (III) acetoacetate (521 mg, 1.47 mmol) stirring under nitrogen at RT. The reaction mixture is concentrated to remove most of the THF and quenched with water. The aqueous layer is extracted with ethyl acetate. The combined organics are washed sequentially with water and saturated aqueous NaCl, dried over Na$_2$SO$_4$, filtered, and concentrated under reduced pressure to give crude product. The crude product is purified by flash chromatography on silica, eluting with 15% hexanes/ethyl acetate. The pure chromatography fractions are combined and concentrated under reduced pressure to give the title compound (0.53 g, 37% yield). LC-ES/MS (m/z): 147.2 (M+H).

Preparation 42

1-(2-ethyl-6-methylpyridin-4-yl)methanamine Dihydrochloride

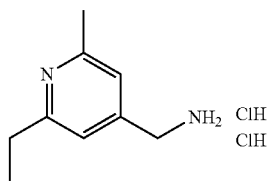

Scheme 4, step B: A solution of 2-ethyl-6-methylpyridine-4-carbonitrile (0.37 g, 2.5 mmol) in 2M NH$_3$ (2 mol/1) in MeOH (12.5 mL) is added to a suspension of Raney nickel (0.5 g) in 2M NH$_3$ in MeOH (12.5 mL). The reaction vessel is purged with nitrogen, and H$_2$ (60 psi) is introduced, with shaking of the subsequent reaction mixture at 40° C. for 15 minutes. The reaction mixture is re-pressurized with H$_2$ (60 psi) and continued to shake for 4 hr. The reaction mixture is filtered. The crude material is diluted with excess 3N HCl in MeOH and concentrated to give a green oil. The crude oil is triturated and concentrated sequentially in the following solvents: toluene, acetonitrile, methanol/toluene and acetonitrile/toluene, to give the title compound as a green solid (0.56 g, 94% yield) after solvent removal. LC-ES/MS (m/z): 151.0 (M+H).

Preparation 43

2-cyclobutyl-6-methyl-pyridine-4-carbonitrile

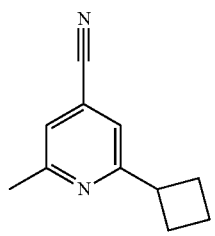

Scheme 4, step A: Add cyclobutylzinc bromide (0.5M in THF, 3.28 mmol) drop wise to a degassed solution of 2-chloro-6-methyl-pyridine-4-carbonitrile (250 mg, 1.64 mmol) and [1,1'-bis(diphenylphosphino)ferrocene]dichloropalladium(II) (122 mg, 0.164 mmol) in 1,4-dioxane. Heat to 80° C. for 1 hr then cool to RT. Add water (5 mL) and stir rapidly for 5 minutes. Remove the solids by filtration through diatomaceous earth. Wash with EtOAc and separate the layers. Wash the organic layer with water and saturated aqueous NaCl. Dry over Na$_2$SO$_4$, filter, and concentrate under reduced pressure. Purify the resulting residue by flash chromatography on silica gel, eluting with a gradient of 10-30% EtOAc in heptane, to give the title compound (232 mg, 82%), after solvent evaporation. LC-ES/MS (m/z): 173.0 (M+H).

Preparation 44

(2-cyclobutyl-6-methyl-4-pyridyl)methanamine Dihydrochloride

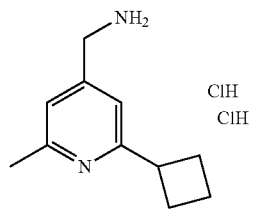

Scheme 4, step B: Prepare the title compound essentially by the method described in Preparation 42, using 2-cyclobutyl-6-methyl-pyridine-4-carbonitrile. LC-ES/MS (m/z): 177.0 (M+H).

Preparation 45

2-cyclopentyl-6-methyl-pyridine-4-carbonitrile

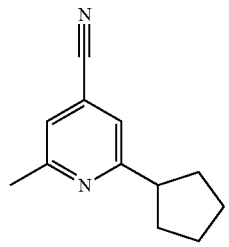

Scheme 4, step A: Prepare the title compound essentially by the method described in Preparation 43, using cyclopentylzinc bromide. $^1$H NMR (CDCl$_3$): δ 1.62-1.78 (m, 4H), 1.78-1.89 (m, 2H), 2.00-2.14 (m, 2H), 2.57 (s, 3H), 3.09-3.25 (m, 1H), 7.16 (s, 1H), 7.19 (s, 1H).

Preparation 46

(2-cyclopentyl-6-methyl-4-pyridyl)methanamine Dihydrochloride

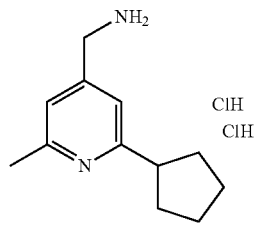

Scheme 4, step B: Prepare the title compound essentially by the method described in Preparation 42, using 2-cyclopenyl-6-methyl-pyridine-4-carbonitrile. LC-ES/MS (m/z): 191.0 (M+H).

Example 1

First Procedure

N-[(2,6-dimethylpyridin-4-yl)methyl]-4-{(1R)-1-[(3S)-3-methyl-2,5-dioxopyrrolidin-3-yl]ethyl}benzamide

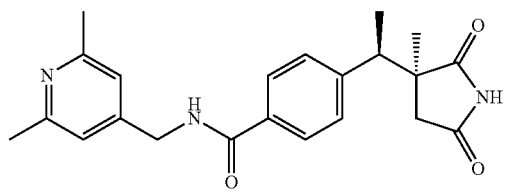 [SMILES: Cc1cc(CNC(=O)c2ccc([C@@H](C)[C@]3(C)CC(=O)NC3=O)cc2)cc(C)n1]

Scheme 1, step F: To a solution of 4-{(1R)-1-[(3S)-3-methyl-2,5-dioxopyrrolidin-3-yl]ethyl}benzoic acid (1.20 g, 4.59 mmol), 1-(2,6-dimethylpyridin-4-yl)methamine dihydrochloride (1.15 g, 5.51 mmol), EDCI (1.08 g, 5.51 mmol), HOBt (768 mg, 5.51 mmol), and DMF (25 mL) is added TEA (2.59 mL, 18.4 mmol). After stirring at RT for 16 hr, water is added, and the mixture extracted with DCM (2×75 mL). The organic layer is dried over Na$_2$SO$_4$, filtered, and concentrated under reduced pressure to give an oil which is purified by flash chromatography on silica, eluting with DCM/MeOH (gradient from 1:0 to 9:1) to obtain the title compound (1.56 g, 89% yield), after solvent evaporation. LC-ES/MS (m/z): 380.2 (M+H). $[α]_D^{20}$=−38.08° (c=1.0, MeOH).

Example 1

Second Procedure

To a suspension of 4-{(1R)-1-[(3S)-3-methyl-2,5-dioxopyrrolidin-3-yl]ethyl}benzoic acid (9.3 g, 36.0 mmol) and 1-(2,6-dimethylpyridin-4-yl)methamine dihydrochloride (7.8 g, 37.0 mmol) in anhydrous DMF (100 mL) is added DIPEA (2.25 mL, 210 mmol) followed by BOP (17.5 g, 39 mmol) in small portions over 10 min, The resulting mixture is stirred at RT for 80 min, poured into 1500 mL ice/water and stirred vigorously. The pH is adjusted to ~7-8 with 5.0 N HCl and the mixture left to stir at RT overnight, extracted with MTBE, and the organic phase is washed with water, dried over Na$_2$SO$_4$, filtered, and concentrated in vacuo and purified by flash chromatography on silica, eluting with 10% methanol/ethyl acetate in hexanes (gradient from 3:5 to 1:0) and the fractions containing product are combined and evaporated in vacuo. The resulting residue is slurried in water (150 mL) for 1.5 days, and the subsequent white solid is collected by filtration and dried under vacuum to obtain the title compound (9.8 g, 73% yield) as a fine white powder. LC-ES/MS (m/z): 380.2 (M+H).

Example 1

Third Procedure

Scheme 2, step I: A mixture of (3S)-3-[(1R)-1-(4-bromophenyl)ethyl]-3-methyl-pyrrolidine-2,5-dione (120 g, 401.1 mmol), (2,6-dimethyl-4-pyridyl)methanamine dihydrochloride (100 g, 481.3 mmol), palladium(II) acetate (2.97 g, 13.24 mmol), 4,5-bis(diphenylphosphino)-9,9-dimethylxanthene (14.85 g, 25.67 mmol), DIPEA (181 g, 1404 mmol) and toluene (1.2 L) is combined in a steel reaction vessel, purged with $N_2$, sealed under an atmosphere of carbon monoxide at 60 psi (401.1 mmol), and heated to 100° C. for 18 h. The reaction mixture is cooled to RT and purged with $N_2$ four times. A little MeOH and DCM are added and the mixture is filtered through pad of diatomaceous earth. The filtrate is concentrated under reduced pressure to give a dark brown oil. DCM (1.5 L) and $H_2O$ (1.5 L) are added, and the resulting brown solid is collected by filtration and triturated with $Et_2O$ to give the title compound as an off white solid (124.8 g, 92% yield). LC-ES/MS (m/z): 380.2 (M+H).

X-Ray Powder Diffraction (XRPD)

The XRD patterns of crystalline solids are obtained on a Bruker D4 Endeavor X-ray powder diffractometer, equipped with a CuKa source (λ=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #38, National Formulary #35 Chapter <941> *Characterization of crystalline and partially crystalline solids by X-ray powder diffraction (XRPD)*, Official May 1, 2015. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, were adjusted based on NIST 675 standard peaks at 8.85 and 26.77 degrees 2θ.

Crystalline Form of Example 1

N-[(2,6-dimethylpyridin-4-yl)methyl]-4-{(1R)-1-[(3S)-3-methyl-2,5-dioxopyrrolidin-3-yl]ethyl}benzamide (crystalline anhydrate)

The compound of example 1, N-[(2,6-dimethylpyridin-4-yl)methyl]-4-{(1R)-1-[(3S)-3-methyl-2,5-dioxopyrrolidin-3-yl]ethyl}benzamide, may be crystallized as an anhydrate of the free base by dissolving N-[(2,6-dimethylpyridin-4-yl)methyl]-4-{(1R)-1-[(3S)-3-methyl-2,5-dioxopyrrolidin-3-yl]ethyl}benzamide (150 mg, 0.40 mmol) in 3 mL of 1:1 methanol:water at 70° C. to give a nearly clear solution. The mixture is cooled to RT and stirred, whereupon a thick white slurry of solids may be observed after 2 hr. The solids are filtered an dried under vacuum at 70° C. for 2 h to obtain the desired title compound crystalline anhydrate (126 mg, 84% yield).

Thus, a prepared sample of N-[(2,6-dimethylpyridin-4-yl)methyl]-4-{(1R)-1-[(3S)-3-methyl-2,5-dioxopyrrolidin-3-yl]ethyl}benzamide (crystalline anhydrate) is characterized by an XRPD pattern using CuKa radiation as having diffraction peaks (2θ values) as described in Table 1 below. Specifically the pattern contains a peak at 13.4° in combination with one or more of the peaks selected from the group consisting of 14.4°, 18.1°, 19.4°, 20.9°, 21.2°, 21.5° and 26.5° with a tolerance for the diffraction angles of 0.2 degrees.

TABLE 1

X-ray powder diffraction peaks of crystalline anhydrate form of Example 1

| Peak | Angle (2-Theta °) | Intensity (%) |
|------|-------------------|---------------|
| 1    | 13.4              | 100           |
| 2    | 14.4              | 74            |
| 3    | 16.3              | 11            |
| 4    | 18.1              | 45            |
| 5    | 19.4              | 49            |
| 6    | 20.6              | 11            |
| 7    | 20.9              | 30            |
| 8    | 21.2              | 37            |
| 9    | 21.5              | 51            |
| 10   | 21.7              | 20            |
| 11   | 23.1              | 14            |
| 12   | 24.1              | 17            |
| 13   | 24.6              | 22            |
| 14   | 25.4              | 14            |
| 15   | 26.5              | 25            |
| 16   | 28.0              | 13            |
| 17   | 30.8              | 11            |

Example 1A

First Procedure

Crystalline N-[(2,6-dimethylpyridin-4-yl)methyl]-4-{(1R)-1-[(3S)-3-methyl-2,5-dioxopyrrolidin-3-yl]ethyl}benzamide methanesulfonate

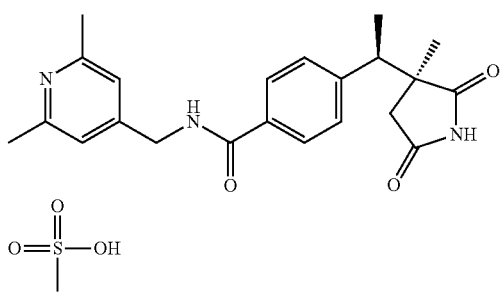

N-[(2,6-dimethylpyridin-4-yl)methyl]-4-{(1R)-1-[(3S)-3-methyl-2,5-dioxopyrrolidin-3-yl]ethyl}benzamide methanesulfonate (509 mg, 1.34 mmol) is slurried in 5 mL of acetone at 1000 rpm/60° C. Methanesulfonic acid (105 μL, 1.6 mmol) is added, and the mixture is stirred to give a clear yellow solution with some gum on the bottom of the vial. The sample is slurried for about 10 min, and some of the gum dissolves before the mixture becomes cloudy and a white solid precipitates out of solution. Heat is removed after another 20 min of stirring, and the sample is stirred at 1000 rpm while cooling to RT. The resulting white solid is isolated by vacuum filtration, rinsed with 500 µL of acetone, and dried on the filter paper for 15 min under an air stream to obtain the title compound (605 mg, 94.8% yield) as a white crystalline solid.

Example 1A

Second Procedure

A solution of N-[(2,6-dimethyl-4-pyridyl)methyl]-4-[(1R)-1-[(3S)-3-methyl-2,5-dioxo-pyrrolidin-3-yl]ethyl] benzamide (23.6 g, 62.2 mmol) in acetone (500 mL) is heated at reflux while stirring at 1000 rpm for 1 hr. Methanesulfonic acid (4.5 mL, 69 mmol) is added and the mixture is heated for 1 hr. After cooling to RT, the resulting precipitate is collected by filtration, washed with acetone, and dried under vacuum to obtain the title compound as an off white powder (28.3 g, 96% yield). LC-ES/MS (m/z): 380.2 (M+H). $^1$H NMR (DMSO): 1.07 (s, 3H), 1.22 (d, 3H), 2.15 (d, 1H), 2.32 (s, 3H), 2.66 (s, 6H), 3.05 (d, 1H), 3.12 (q, 1H), 4.62 (d, 2H), 7.43 (d, 2H), 7.62 (s, 2H), 7.87 (d, 2H), 9.24 (bt, 1H), 11.24 (bs, 1H). Chiral analysis: >99% de, $t_R$=2.32 min (Chiral SFC OD-H column, 17% EtOH in 20 mM NH$_3$/MeOH, 5 mL/min, 100 bar, 35° C., 220 nm).

A sample of crystalline N-[(2,6-dimethylpyridin-4-yl)methyl]-4-{(1R)-1-[(3S)-3-methyl-2,5-dioxopyrrolidin-3-yl]ethyl}benzamide methanesulfonate is characterized by an XRD pattern using CuKa radiation as having diffraction peaks (2θ values) as described in Table 2 below, and in particular having peaks at 18.8° in combination with one or more of the peaks selected from the group consisting of 23.2°, 24.7°, and 15.2°; with a tolerance for the diffraction angles of 0.2 degrees.

TABLE 2

X-ray powder diffraction peaks of Example 1A

| Peak | Angle (2-Theta °) | Intensity (%) |
|---|---|---|
| 1 | 10.3 | 6.4% |
| 2 | 10.9 | 6.7% |
| 3 | 11.7 | 11.1% |
| 4 | 12.6 | 9.6% |
| 5 | 15.2 | 20.6% |
| 6 | 16.2 | 17.1% |
| 7 | 18.8 | 100.0% |
| 8 | 21.0 | 14.3% |
| 9 | 23.2 | 43.3% |
| 10 | 24.7 | 27.7% |

Example 2

N-[(4,6-dimethyl-2-pyridyl)methyl]-4-[(1 R)-1-[(3S)-3-methyl-2,5-dioxo-pyrrolidin-3-yl]ethyl]benzamide

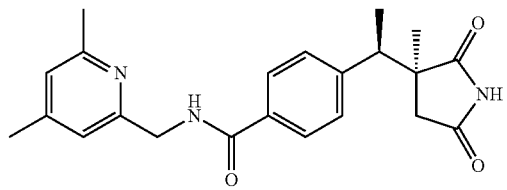 [SMILES: Cc1cc(C)nc(CNC(=O)c2ccc([C@@H](C)[C@]3(C)CC(=O)NC3=O)cc2)c1]

Scheme 7, step A (X=CH, Y=N, Z=CH, R=Me): Prepare from 1-(4,6-dimethylpyridin-2-yl)methanamine (Aldrich, CAS#76457-15-3, 30 mg, 0.21 mmol) and 4-[(1R)-1-[(3S)-3-methyl-2,5-dioxo-pyrrolidin-3-yl]ethyl]benzoic acid (45 mg, 0.17 mmol) essentially by the method described in Example 1: First Procedure to obtain the title compound (61 mg, 93% yield). LC-ES/MS (m/z): 380.0 (M+H).

Example 3

N-[(6-cyano-4-methyl-2-pyridyl)methyl]-4-[(1R)-1-[(3S)-3-methyl-2,5-dioxo-pyrrolidin-3-yl]ethyl]benzamide

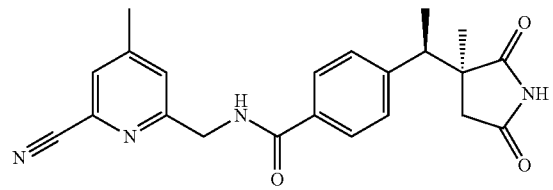 [SMILES: Cc1cc(C#N)nc(CNC(=O)c2ccc([C@@H](C)[C@]3(C)CC(=O)NC3=O)cc2)c1]

Scheme 7, step A (X=CH, Y=N, Z=CH, R=CN): Prepare from 6-(aminomethyl)-4-methyl-pyridine-2-carbonitrile (35 mg, 0.23 mmol) and 4-[(1R)-1-[(3S)-3-methyl-2,5-dioxo-pyrrolidin-3-yl]ethyl]benzoic acid (50 mg, 0.191 mmol) essentially by the method described in Example 1: First Procedure to obtain the title compound (36 mg, 48% yield). LC-ES/MS (m/z): 391.0 (M+H).

Example 4

N-[(2-cyano-6-methyl-4-pyridyl)methyl]-4-[(1R)-1-[(3S)-3-methyl-2,5-dioxo-pyrrolidin-3-yl]ethyl]benzamide

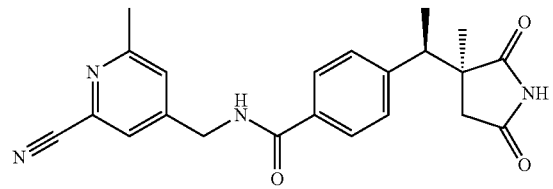 [SMILES: Cc1cc(CNC(=O)c2ccc([C@@H](C)[C@]3(C)CC(=O)NC3=O)cc2)cc(C#N)n1]

Scheme 7, step A (X=CH, Y=CH, Z=N, R=CN): Prepare from 4-(aminomethyl)-6-methyl-pyridine-2-carbonitrile (53 g, 0.289 mmol) and 4-[(1R)-1-[(3S)-3-methyl-2,5-dioxo-pyrrolidin-3-yl]ethyl]benzoic acid (50 mg, 0.19 mmol)

essentially by the method described in Example 1: First Procedure to obtain the title compound (52 g, 69% yield). LC-ES/MS (m/z): 391.0 (M+H).

Example 5

N-[(2-isopropyl-6-methyl-4-pyridyl)methyl]-4-[(R)-1-[(3S)-3-methyl-2,5-dioxo-pyrrolidin-3-yl]ethyl]benzamide

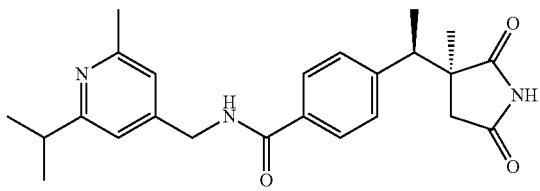 [SMILES: Cc1cc(CNC(=O)c2ccc([C@@H](C)[C@]3(C)CC(=O)NC3=O)cc2)cc(C(C)C)n1]

Scheme 7, step A (X=CH, Y=CH, Z=N, R=i-Pr): Prepare from (2-isopropyl-6-methyl-4-pyridyl)methanamine (42 mg, 0.23 mmol) and 4-[(1R)-1-[(3S)-3-methyl-2,5-dioxo-pyrrolidin-3-yl]ethyl]benzoic acid (50 mg, 0.19 mmol) essentially by the method described in Example 1: First Procedure to obtain the title compound (60 mg, 77% yield). LC-ES/MS (m/z): 408.2 (M+H).

Example 6

N-[(2-cyclopropyl-6-methyl-4-pyridyl)methyl]-4-[(1R)-1-[(3S)-3-methyl-2,5-dioxo-pyrrolidin-3-yl]ethyl]benzamide

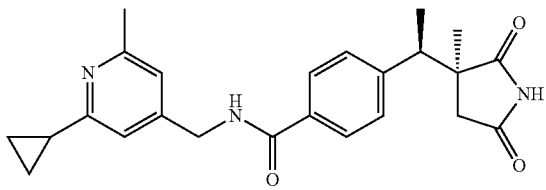 [SMILES: Cc1cc(CNC(=O)c2ccc([C@@H](C)[C@]3(C)CC(=O)NC3=O)cc2)cc(C2CC2)n1]

Scheme 7, step A (X=CH, Y=CH, Z=N, R=c-Pr): Prepare from (2-cyclopropyl-6-methyl-4-pyridyl)methanamine dihydrochloride (54 mg, 0.23 mmol) and 4-[(1R)-1-[(3S)-3-methyl-2,5-dioxo-pyrrolidin-3-yl]ethyl]benzoic acid (50 mg, 0.19 mmol) essentially by the method described in Example 1: First Procedure to obtain the title compound (0.068 g, 88% yield). LC-ES/MS (m/z): 406.2 (M+H).

Example 7

N-[(6-cyclopropyl-4-methyl-2-pyridyl)methyl]-4-[(1R)-1-[(3S)-3-methyl-2,5-dioxo-pyrrolidin-3-yl]ethyl]benzamide

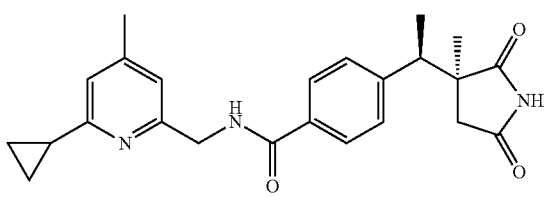 [SMILES: Cc1cc(CNC(=O)c2ccc([C@@H](C)[C@]3(C)CC(=O)NC3=O)cc2)nc(C2CC2)c1]

Scheme 7, step A (X=CH, Y=N, Z=CH, R=c-Pr): Prepare from (6-cyclopropyl-4-methyl-2-pyridyl)methanamine dihydrochloride (54 mg, 0.23 mmol) and 4-[(1R)-1-[(3S)-3-methyl-2,5-dioxo-pyrrolidin-3-yl]ethyl]benzoic acid (50 mg, 0.19 mmol) essentially by the method described in Example 1: First Procedure to obtain the title compound (64 g, 83% yield). LC-ES/MS (m/z): 406.2 (M+H).

Example 8

N-[(2,6-dimethyl-4-pyridyl)methyl]-5-[(1R)-1-[(3S)-3-methyl-2,5-dioxo-pyrrolidin-3-yl]ethyl]pyridine-2-carboxamide

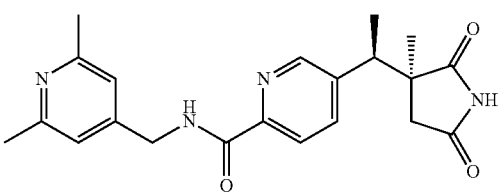 [SMILES: Cc1cc(CNC(=O)c2ccc([C@@H](C)[C@]3(C)CC(=O)NC3=O)cn2)cc(C)n1]

Scheme 7, step A (X=N, Y=CH, Z=N, R=Me): Methyl 5-[(1R)-1-[(3S)-3-methyl-2,5-dioxo-pyrrolidin-3-yl]ethyl]pyridine-2-carboxylate (110 mg, 0.39 mmol), (2,6-dimethylpyridin-4-yl)methanamine (Aurora Building Blocks, CAS #324571-98-4, 83 mg, 0.59 mmol), and toluene (10 mL) are heated at 150° C. for 2 days and at 165° C. for one day. The reaction mixture is cooled and concentrated. The crude product is purified by flash chromatography on silica, eluting with DCM/MeOH (gradient from 99:1 to 92:8). The pure chromatography fractions are combined and concentrated under reduced pressure to give the title compound (64 mg, 42% yield). LC-ES/MS (m/z): 381.0 (M+H).

Example 9

N-[(2-cyclopropyl-6-methyl-4-pyridyl)methyl]-5-[(1R)-1-[(3S)-3-methyl-2,5-dioxo-pyrrolidin-3-yl]ethyl]pyridine-2-carboxamide

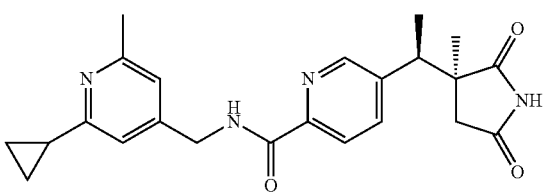

Scheme 7, step A (X=N, Y=CH, Z=N, R=c-Pr): Methyl 5-[(1R)-1-[(3S)-3-methyl-2,5-dioxo-pyrrolidin-3-yl]ethyl]pyridine-2-carboxylate (100 mg, 0.36 mmol), (2-cyclopropyl-6-methyl-4-pyridyl)methanamine dihydrochloride (126 mg, 0.54 mmol), triethylamine (0.15 mL, 1.07 mmol) and toluene (3 mL) are heated in a microwave at 170° C. for 1 hour and in an oil bath at 160° C. for 20 hours. The reaction mixture is cooled and concentrated. The crude product is purified by flash chromatography on silica, eluting with DCM/MeOH (gradient from 99:1 to 92:8). The pure chromatography fractions are combined and concentrated under reduced pressure to give the title compound (34 mg, 23% yield). LC-ES/MS (m/z): 407.0 (M+H).

Example 10

N-[(2-ethyl-6-methylpyridin-4-yl)methyl]-4-{(1R)-1-[(3S)-3-methyl-2,5-dioxopyrrolidin-3-yl]ethyl}benzamide

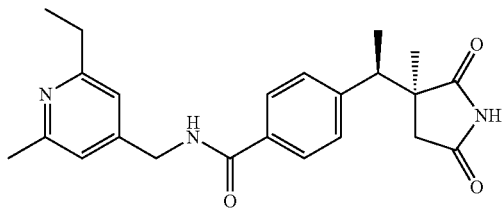 [SMILES: CCc1cc(CNC(=O)c2ccc([C@@H](C)[C@]3(C)CC(=O)NC3=O)cc2)cc(C)n1]

Scheme 7, step A (X=CH, Y=CH, Z=N, R=Et): To a solution 4-{(1R)-1-[(3S)-3-methyl-2,5-dioxopyrrolidin-3-yl]ethyl}benzoic acid (40 mg, 0.153 mmol) in DMF (0.76 mL) is added 1-(2-ethyl-6-methylpyridin-4-yl)methanamine dihydrochloride (51 mg, 0.23 mmol), DIPEA (0.15 mL, 0.92 mmol), and HATU (71 mg, 0.18 mmol) at RT. After 17 hr, the reaction mixture is purified by reverse phase chromatography (PHENOMENEX® GEMINI®-NX C18 column) eluting with 10 mmol ammonium bicarbonate (pH~10 with 5% methanol) and ACN to give the title compound (43.0 mg, 71% yield), after solvent evaporation. LC/MS (m/z): 394.4 (M+H).

Example 11

N-[(2-cyclobutyl-6-methylpyridin-4-yl)methyl]-4-{(1R)-1-[(3S)-3-methyl-2,5-dioxopyrrolidin-3-yl]ethyl}benzamide

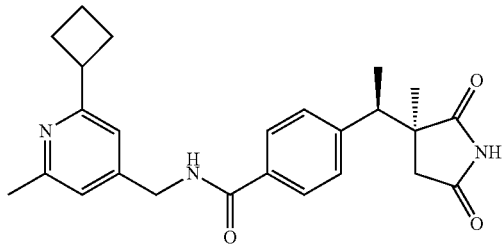 [SMILES: Cc1cc(CNC(=O)c2ccc([C@@H](C)[C@]3(C)CC(=O)NC3=O)cc2)cc(C2CCC2)n1]

Scheme 7, step A (X=CH, Y=CH, Z=N, R=c-Bu): Prepare from 4-{(1R)-1-[(3S)-3-methyl-2,5-dioxopyrrolidin-3-yl]ethyl}benzoic acid (40 mg, 0.15 mmol) and (2-cyclobutyl-6-methyl-4-pyridyl)methanamine dihydrochloride (57 mg, 0.23 mmol) essentially by the method described in Example 10 to give the title compound (38 mg, 60% yield). LC/MS (m/z): 420.2 (M+H).

Example 12

N-[(2-cyclopentyl-6-methylpyridin-4-yl)methyl]-4-{(1R)-1-[(3S)-3-methyl-2,5-dioxopyrrolidin-3-yl]ethyl}benzamide

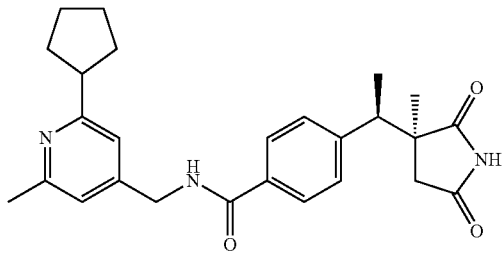 [SMILES: Cc1cc(CNC(=O)c2ccc([C@@H](C)[C@]3(C)CC(=O)NC3=O)cc2)cc(C2CCCC2)n1]

Scheme 7, step A (X=CH, Y=CH, Z=N, R=c-pentyl): Prepare from 4-{(1R)-1-[(3S)-3-methyl-2,5-dioxopyrrolidin-3-yl]ethyl}benzoic acid (40 mg, 0.15 mmol) and (2-cyclopentyl-6-methyl-4-pyridyl)methanamine dihydrochloride (60 mg, 0.23 mmol) essentially by the method described in Example 10 to give the title compound (47.7 mg, 72% yield). LC/MS (m/z): 434.2 (M+H).

Inhibition of cAMP Production by CGRP Receptor Antagonists

The hCGRP (human calcitonin gene-related peptide) receptor is functionally coupled to the Gas proteins. Stimulation of hCGRP results in an increased synthesis of intracellular cAMP and can be blocked by the addition of receptor antagonists. Receptor activity is thus a reflection of the amount of cAMP present within cells which can be detected using standard in vitro technology.

Cell Culture:

Cultured SK-N-MC neuroblastoma cells (ATCC® HTB-10™) that endogenously express the hCGRP receptor are grown in Eagle's Minimum essential medium (HYCLONE™) supplemented with 10% heat-inactivated Fetal bovine serum (FBS; GIBCO®), Non-Essential Amino Acids (GIBCO®), 1 mM sodium pyruvate, 2 mM L-glutamine, 100 U/mL of penicillin, and 10 µg/mL of streptomycin to about 70% confluency. After providing fresh medium, the cells are incubated at 37° C. overnight. On the day of the assay, cells are detached using ACCUTASE® (MP Biomedicals), resuspended in assay buffer [Hank's Balanced Salt Solution/Dulbecco's phosphate-buffered saline with 100 mg/mL each of $CaCl_2$ and $MgCl_2$ mixed 1:2, 3.3 mM 4-(2-hydroxyethyl)-1-piperazineethanesulfonic acid, 0.03% bovine serum albumin, and 0.5 mM 1-methyl-3-isobutylxanthine (as inhibitor of cAMP)], and seeded 3-5K/well into 384-well, poly-D-lysine coated white plates (BD Biosciences).

Inhibition of cAMP Production:

For dose-response studies, compounds are serially diluted 1:3 in dimethyl sulfoxide and then 1:10 into assay buffer. Human CGRP (0.8 nM; Bachem) as a receptor-specific agonist for the hCGRP receptor is mixed with diluted compound and added to the cells as the challenge stimulant at their $EC_{80}$ concentrations.

Data Analysis:

The amount of intracellular cAMP is quantitated using HTRF technology (Cisbio) as per vendor instructions. Briefly, cAMP-d2 conjugate and anti-cAMP-cryptate conjugate in lysis buffer are incubated with the treated cells at RT for 90 min. The HTRF signal is immediately detected using an ENVISION® plate reader (Perkin-Elmer) to calculate the ratio of fluorescence at 665 to 620 nM. The raw data are converted to cAMP amount (pmole/well) using a cAMP standard curve generated for each experiment. Relative $EC_{50}$ values are calculated from the top-bottom range of the concentration response curve using a four-parameter logistic curve fitting program (ACTIVITYBASE® v5.3.1.22 or GENEDATA SCREENER® v12.0.4), and $K_b$ values are estimated as agonist-corrected $IC_{50}$ values using the equation:

$$K_b = (IC_{50})/[1+([Agonist]/EC_{50})].$$

Estimated $K_b$ values are reported as mean values±SEM, averaged from the number of runs (n).

Following the procedure essentially as described above, the compounds of Examples 1-12 have a $K_b$ measured at human CGRP as shown in Table 3. This demonstrates that the compounds of Examples 1-12 are antagonists of the human CGRP receptor in vitro.

TABLE 3

Measured Kb at human CGRP receptor in vitro

| Example Number | Kb hCGRP (nM) | n (number of runs) |
|---|---|---|
| 1 | 0.546 ± 0.226 | 7 |
| 2 | 2.22 ± 1.47 | 8 |
| 3 | 1.51 ± 0.140 | 4 |
| 4 | 23.5 ± 0.925 | 2 |
| 5 | 0.718 ± 0.0045 | 2 |
| 6 | 0.375 ± 0.172 | 6 |
| 7 | 0.582 ± 0.228 | 3 |
| 8 | 1.25 ± 0.0045 | 2 |
| 9 | 1.15 ± 0.181 | 2 |
| 10 | 0.60 ± 0.0431 | 2 |
| 11 | 0.110 ± 0.011 | 2 |
| 12 | 0.295 ± 0.056 | 3 |

CGRP (Calcitonin Gene-Related Peptide)
Non-Human Primates Studies

Capsaicin-induced dermal blood flow (DBF) may be used as a target engagement biomarker to assess CGRP receptor activity in nonhuman primates (NHPs). Methods are adapted from earlier published procedures [Hershey et al., *Regulatory Peptides*, Volume 127, Issue 1-3, pp. 71-77, 2005].

Study Population:

Animal studies may be performed under protocols approved by the Covance Institutional Animal Care and Use Committee. Cynomolgus NHPs may be used given the close homology between NHP and human CGRP receptor. The study population may include healthy, CGRP antagonist naive cynomolgus NHP males weighing ~3-4 kg.

Cynomolgus NHPs are enrolled in the study based on prescreening for capsaicin responsiveness. NHPs that exhibited ≥50% increase in blood flow over baseline with 2 mg (20 μL/ring) topical capsaicin treatment (average of 3 O-rings) over baseline in response to capsaicin in the screened arm and stable physiology during the imaging period are included in a study with the compound of Example 1. NHPs are used in a cross over design in which all NHPs received all doses after a two week wash-out period. Total n=10 NHPs per group.

Dose Administration.

NHPs each receive vehicle, 0/3 3 and 30 mg/kg of the antagonist Example 1 administered orally (10% Acacia w/v/0.05% Antifoam 1510-US v/v/in PW) 90 min prior to the capsaicin administration in the laser Doppler imaging (LDI) experiment.

Pharmacodynamic Sampling.

Animals are fasted overnight prior to each capsaicin challenge. On the day of the experiment, the NHPs are anesthetized with 1% Isoflurane for approximately 30 min prior to scanning. The NHPs are placed in a quiet, temperature-controlled room supine on a warm small surgical blanket and the shaved arm is placed on a heating pad under the laser head. Three neoprene O-rings (size=8 mm ID) are placed on the NHP forearm, approximately 1 cm apart. During a 30-min stabilization period, preliminary scans are obtained to confirm correct positioning of the O-rings. Once baseline temperature (approximately 37° C.) is stabilized, a baseline scan is collected. After the baseline scan is completed, 20 μl of capsaicin solution (50 mg of capsaicin in a solution of 170 μl EtOH, 80 μl TWEEN® 20, 250 μl purified H2O) is applied to each O-ring. Scanning is continued every 5 min for an additional 25 min (85, 90, 95, 100, 105, 110, 115, and 120 min post-treatment with CGRP receptor antagonist compound).

Analysis and Statistics: LDI repeat scans are analyzed using Moor software v.5.2 (Moor Instruments, Wilmington, Del.) by region of interest signal analysis, and Microsoft Excel worksheets are used for averaging the signal from the regions of interest at a given time point. Changes in DBF are reported as percent change from baseline DBF. Analyzed data is entered into Graphpad PRISM® 4.0 for graphing and a repeated measurement mixed-effect model in SAS® 9.1 is used for statistical analysis. Data is expressed as mean+/− SD.

Using a mixed effect model with repeated measurement (autoregressive correlation via AR1 process) and false discovery rate multiple adjustments, compared to vehicle the compound of Example 1 at 3 and 30 mg/kg gives statistically significant decreased blood flow increase following a capsaicin challenge with group mean inhibition of 27.4% ($p<0.003$) and 40.6% ($p<0.00001$) respectively.

We claim:

1. A compound of the formula:

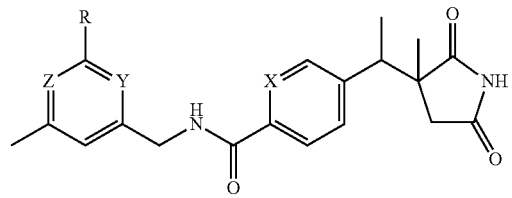

wherein

Y is CH or N;

Z is CH or N;

provided that when Y is CH, Z is N and when Y is N, Z is CH;

X is CH or N; and

R is C1-C3 alkyl, C3-C5 cycloalkyl, or CN, or a pharmaceutically acceptable salt thereof.

2. The compound or salt according to claim 1 wherein X is CH.

3. The compound or salt according to claim 2 wherein Y is CH and Z is N.

4. The compound or salt according to claim 3 wherein R is C1-C3 alkyl.

5. The compound or salt according to claim 4 of the Formula:

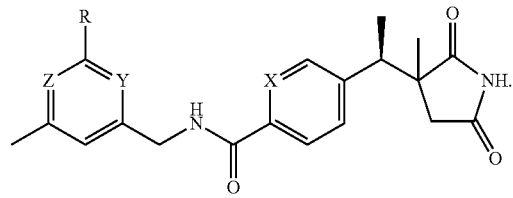

6. The compound or salt according to claim 5 of the Formula:

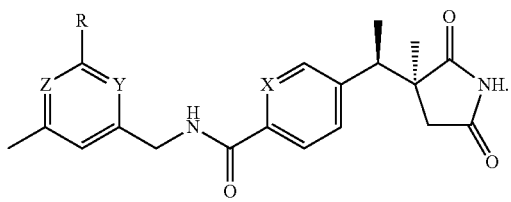

7. The compound or salt according to claim 1 wherein the compound is:

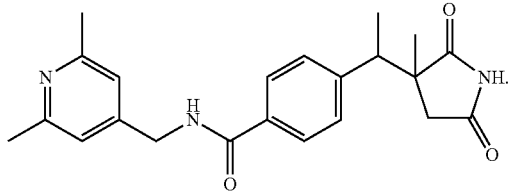 [SMILES: Cc1cc(CNC(=O)c2ccc(C(C)C3(C)CC(=O)NC3=O)cc2)cc(C)n1]

8. The compound or salt according to claim 7 wherein the compound is:

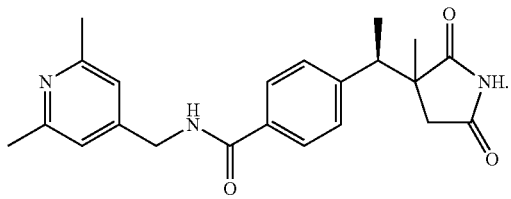 [SMILES: Cc1cc(CNC(=O)c2ccc([C@@H](C)C3(C)CC(=O)NC3=O)cc2)cc(C)n1]

9. The compound or salt according to claim 8 wherein the compounds is:

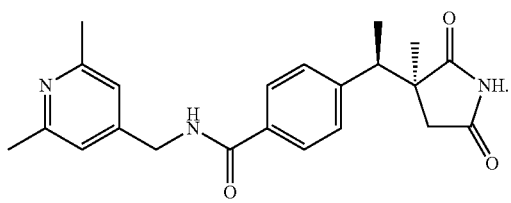 [SMILES: Cc1cc(CNC(=O)c2ccc([C@@H](C)[C@]3(C)CC(=O)NC3=O)cc2)cc(C)n1]

10. The compound according to claim 9 which is:

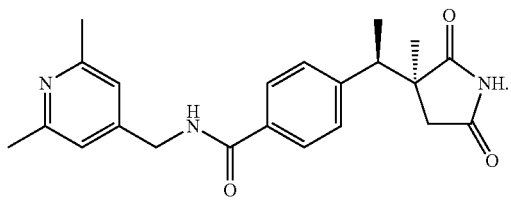 [SMILES: Cc1cc(CNC(=O)c2ccc([C@@H](C)[C@]3(C)CC(=O)NC3=O)cc2)cc(C)n1]

11. The compound according to claim 10 which is a crystalline anhydrate.

12. The compound according to claim 11 which is characterized by a substantial peak in the X-ray diffraction spectrum at diffraction angle 2-theta of 13.4°, in combination with one or more of the peaks selected from the group consisting of 14.4°, 18.1°, 19.4°, 20.9°, 21.2°, 21.5° and 26.5°, with a tolerance for the diffraction angles of 0.2 degrees.

13. The salt according to claim 9 which is:

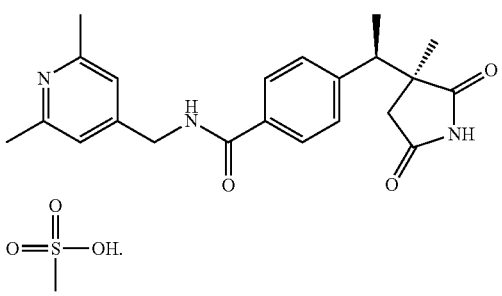

14. The salt according to claim 13 which is crystalline.

15. The salt according to claim 14 which is characterized by a substantial peak in the X-ray diffraction spectrum at diffraction angle 2-theta of at 18.8° in combination with one or more of the peaks selected from the group consisting of 23.2°, 24.7°, and 15.2°; with a tolerance for the diffraction angles of 0.2 degrees.

16. A method of preventing migraine in a patient, comprising administering to a patient in need thereof an effective amount of a compound or salt according to claim 1.

17. A method of treating migraine in a patient, comprising administering to a patient in need thereof an effective amount of a compound or salt according to claim 1.

18. A method of preventing migraine in a patient, comprising administering to a patient in need thereof an effective amount of a compound or salt according to claim 9.

19. A method of treating migraine in a patient, comprising administering to a patient in need thereof an effective amount of a compound or salt according to claim 9.

20. A pharmaceutical composition, comprising a compound or salt according to claim 1 with one or more pharmaceutically acceptable carriers, diluents, or excipients.

21. A pharmaceutical composition, comprising a compound or salt according to claim 9 with one or more pharmaceutically acceptable carriers, diluents, or excipients.

22. A process for preparing a pharmaceutical composition, comprising admixing a compound or salt according to claim 1 with one or more pharmaceutically acceptable carriers, diluents, or excipients.

23. A process for preparing a pharmaceutical composition, comprising admixing a compound or salt according to claim 9 with one or more pharmaceutically acceptable carriers, diluents, or excipients.

* * * * *

UNITED STATES PATENT AND TRADEMARK OFFICE
CERTIFICATE OF CORRECTION

| | |
|---|---|
| PATENT NO. | : 9,708,297 B2 |
| APPLICATION NO. | : 15/229249 |
| DATED | : July 18, 2017 |
| INVENTOR(S) | : David Andrew Coates et al. |

It is certified that error appears in the above-identified patent and that said Letters Patent is hereby corrected as shown below:

In the Claims

In Column 55, Line 36 please delete "compounds" and insert -- compound --, therefor.

Signed and Sealed this
Thirty-first Day of October, 2017

Joseph Matal
*Performing the Functions and Duties of the
Under Secretary of Commerce for Intellectual Property and
Director of the United States Patent and Trademark Office*